(12) United States Patent
Siefert

(10) Patent No.: US 9,454,646 B2
(45) Date of Patent: *Sep. 27, 2016

(54) SHORT IMAGERY TASK (SIT) RESEARCH METHOD

(71) Applicant: The Nielsen Company (US), LLC, New York, NY (US)

(72) Inventor: Caleb J. Siefert, Ann Arbor, MI (US)

(73) Assignee: THE NIELSEN COMPANY (US), LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/230,418

(22) Filed: Mar. 31, 2014

(65) Prior Publication Data

US 2014/0214335 A1 Jul. 31, 2014

Related U.S. Application Data

(63) Continuation of application No. 13/089,752, filed on Apr. 19, 2011, now Pat. No. 8,684,742.

(60) Provisional application No. 61/325,794, filed on Apr. 19, 2010.

(51) Int. Cl.
| | |
|---|---|
| *G09B 7/00* | (2006.01) |
| *G06F 19/00* | (2011.01) |
| *G09B 7/073* | (2006.01) |
| *G09B 5/10* | (2006.01) |

(52) U.S. Cl.
CPC .............. *G06F 19/36* (2013.01); *G09B 5/10* (2013.01); *G09B 7/073* (2013.01)

(58) Field of Classification Search
CPC .... G09B 7/07; G09B 7/073; G06Q 30/0201; G06Q 30/0202; G06F 19/36
USPC .................. 434/236, 350; 705/7.29, 7.31
See application file for complete search history.

(56) References Cited

U.S. PATENT DOCUMENTS

| | | |
|---|---|---|
| 2,549,836 A | 4/1951 | McIntyre et al. |
| 3,490,439 A | 1/1970 | Rolston |
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,145,122 A | 3/1979 | Rinard et al. |

(Continued)

FOREIGN PATENT DOCUMENTS

| | | |
|---|---|---|
| EP | 1087618 | 3/2001 |
| EP | 1609418 | 12/2005 |

(Continued)

OTHER PUBLICATIONS

"ARF, AAAA and ANA Are Getting Emotional about Engagement", Presentation, pp. 1-103 (2005).

(Continued)

*Primary Examiner* — Peter Egloff
(74) *Attorney, Agent, or Firm* — Hanley, Flight & Zimmerman, LLC

(57) ABSTRACT

The present invention relates to biologically and behaviorally based methods of measuring audience response to a short stimulus.

21 Claims, 8 Drawing Sheets

(56) References Cited

U.S. PATENT DOCUMENTS

| | | |
|---|---|---|
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,626,904 A | 12/1986 | Lurie |
| 4,632,122 A | 12/1986 | Johansson et al. |
| 4,683,892 A | 8/1987 | Johansson et al. |
| 4,686,999 A | 8/1987 | Snyder et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,870,579 A | 9/1989 | Hey ............................ 705/7.31 |
| 4,885,687 A | 12/1989 | Carey |
| 4,894,777 A | 1/1990 | Negishi et al. |
| 4,913,160 A | 4/1990 | John |
| 4,955,388 A | 9/1990 | Silberstein |
| 4,967,038 A | 10/1990 | Gevins et al. |
| 4,973,149 A | 11/1990 | Hutchinson |
| 4,987,903 A | 1/1991 | Keppel et al. |
| 5,003,986 A | 4/1991 | Finitzo et al. |
| 5,010,891 A | 4/1991 | Chamoun |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy et al. |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. ........... 364/419.2 |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,331,544 A | 7/1994 | Lu et al. |
| 5,339,826 A | 8/1994 | Schmidt et al. |
| 5,345,281 A | 9/1994 | Taboada et al. |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,410,609 A | 4/1995 | Kado et al. |
| 5,436,830 A | 7/1995 | Zatlman .................... 364/419.2 |
| 5,447,166 A | 9/1995 | Gevins |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,537,618 A | 7/1996 | Boulton et al. |
| 5,550,928 A | 8/1996 | Lu et al. |
| 5,617,855 A | 4/1997 | Waletzky et al. |
| 5,655,534 A | 8/1997 | Ilmoniemi |
| 5,676,138 A | 10/1997 | Zawilinski |
| 5,676,148 A | 10/1997 | Koo et al. ................ 128/661.01 |
| 5,687,322 A | 11/1997 | Deaton et al. |
| 5,720,619 A | 2/1998 | Fisslinger |
| 5,724,987 A | 3/1998 | Gevins et al. |
| 5,726,701 A | 3/1998 | Needham |
| 5,729,205 A | 3/1998 | Kwon |
| 5,736,986 A | 4/1998 | Sever, Jr. |
| 5,740,035 A | 4/1998 | Cohen et al. |
| 5,762,611 A | 6/1998 | Lewis et al. |
| 5,771,897 A | 6/1998 | Zufrin |
| 5,774,591 A | 6/1998 | Black et al. |
| 5,787,187 A | 7/1998 | Bouchard et al. |
| 5,800,351 A | 9/1998 | Mann |
| 5,802,208 A | 9/1998 | Podilchuk et al. |
| 5,802,220 A | 9/1998 | Black et al. |
| 5,812,642 A | 9/1998 | Leroy |
| 5,817,029 A | 10/1998 | Gevins et al. |
| 5,842,199 A | 11/1998 | Miller et al. |
| 5,848,399 A | 12/1998 | Burke |
| 5,892,566 A | 4/1999 | Bullwinkel |
| 5,945,863 A | 8/1999 | Coy |
| 5,961,332 A | 10/1999 | Joao |
| 5,983,129 A | 11/1999 | Cowan et al. |
| 5,995,868 A | 11/1999 | Dorfmeister et al. |
| 6,001,065 A | 12/1999 | DeVito |
| 6,016,475 A | 1/2000 | Miller et al. ................. 705/7.29 |
| 6,021,346 A | 2/2000 | Ryu et al. |
| 6,032,129 A | 2/2000 | Greef et al. |
| 6,052,619 A | 4/2000 | John |
| 6,088,040 A | 7/2000 | Oda et al. |
| 6,099,319 A | 8/2000 | Zaltman et al. |
| 6,120,440 A | 9/2000 | Goknar |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,170,018 B1 | 1/2001 | Voll et al. |
| 6,171,239 B1 | 1/2001 | Humphrey |
| 6,173,260 B1 | 1/2001 | Slaney |
| 6,175,753 B1 | 1/2001 | Menkes et al. |
| 6,212,502 B1 | 4/2001 | Ball et al. |
| 6,228,038 B1 | 5/2001 | Claessens |
| 6,236,885 B1 | 5/2001 | Hunter et al. |
| 6,254,536 B1 | 7/2001 | DeVito |
| 6,280,198 B1 | 8/2001 | Calhoun et al. |
| 6,286,005 B1 | 9/2001 | Cannon |
| 6,289,234 B1 | 9/2001 | Mueller |
| 6,292,688 B1 | 9/2001 | Patton |
| 6,299,308 B1 | 10/2001 | Voronka et al. |
| 6,301,493 B1 | 10/2001 | Marro et al. |
| 6,315,569 B1 | 11/2001 | Zaltman |
| 6,330,470 B1 | 12/2001 | Tucker et al. |
| 6,334,778 B1 | 1/2002 | Brown |
| 6,358,201 B1 | 3/2002 | Childre et al. ................ 600/300 |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill .............................. 600/300 |
| 6,434,419 B1 | 8/2002 | Gevins et al. |
| 6,435,878 B1 | 8/2002 | Reynolds et al. |
| 6,453,194 B1 | 9/2002 | Hill |
| 6,453,241 B1 | 9/2002 | Bassett, Jr. et al. |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,545,685 B1 | 4/2003 | Dorbie |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,609,024 B1 | 8/2003 | Ryu et al. |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,688,890 B2 | 2/2004 | von Buegner |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopinathan et al. |
| 6,788,882 B1 | 9/2004 | Geer et al. |
| 6,792,304 B1 | 9/2004 | Silberstein |
| 6,842,877 B2 | 1/2005 | Robarts et al. |
| 6,850,252 B1 | 2/2005 | Hoffberg ....................... 345/716 |
| 6,852,875 B2 | 2/2005 | Prakash ......................... 560/40 |
| 6,888,457 B2 | 5/2005 | Wilkinson et al. ............ 340/540 |
| 6,904,408 B1 | 6/2005 | McCarthy et al. |
| 6,950,698 B2 | 9/2005 | Sarkela et al. |
| 6,958,710 B2 | 10/2005 | Zhang et al. |
| 6,973,342 B1 | 12/2005 | Swanson |
| 6,993,380 B1 | 1/2006 | Modarres |
| 7,043,056 B2 | 5/2006 | Edwards et al. |

(56) References Cited

U.S. PATENT DOCUMENTS

| | | |
|---|---|---|
| 7,047,550 B1 | 5/2006 | Yasukawa et al. |
| 7,113,916 B1 | 9/2006 | Hill |
| 7,120,880 B1 | 10/2006 | Dryer et al. |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,177,675 B2 | 2/2007 | Suffin et al. |
| 7,222,071 B2 | 5/2007 | Neuhauser et al. |
| 7,246,081 B2 | 7/2007 | Hill |
| 7,272,982 B2 | 9/2007 | Neuhauser et al. |
| 7,286,871 B2 | 10/2007 | Cohen |
| 7,340,060 B2 | 3/2008 | Tomkins et al. |
| 7,391,835 B1 | 6/2008 | Gross et al. |
| 7,394,385 B2 | 7/2008 | Franco, Jr. et al. |
| 7,408,460 B2 | 8/2008 | Crystal et al. |
| 7,420,464 B2 | 9/2008 | Fitzgerald et al. |
| 7,443,292 B2 | 10/2008 | Jensen et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,987 B2 | 12/2008 | Crystal et al. |
| 7,483,835 B2 | 1/2009 | Neuhauser et al. |
| 7,483,844 B2 | 1/2009 | Takakura et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,630,757 B2 | 12/2009 | Dorfmeister et al. |
| 7,636,456 B2 | 12/2009 | Collins et al. |
| 7,650,793 B2 | 1/2010 | Jensen et al. |
| 7,658,327 B2 | 2/2010 | Tuchman et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,720,351 B2 | 5/2010 | Levitan |
| 7,729,755 B2 | 6/2010 | Laken |
| 7,765,564 B2 | 7/2010 | Deng |
| 7,774,052 B2 | 8/2010 | Burton et al. |
| 7,797,186 B2 | 9/2010 | Dybus .............. 705/10 |
| 7,809,420 B2 | 10/2010 | Hannula et al. |
| 7,840,248 B2 | 11/2010 | Fuchs et al. |
| 7,840,250 B2 | 11/2010 | Tucker |
| 7,865,394 B1 | 1/2011 | Calloway et al. |
| 7,892,764 B2 | 2/2011 | Xiong et al. |
| 7,908,133 B2 | 3/2011 | Neuhauser |
| 7,917,366 B1 | 3/2011 | Levanon et al. |
| 7,930,199 B1 | 4/2011 | Hill .............. 705/7.29 |
| 7,962,315 B2 | 6/2011 | Jensen et al. |
| 7,988,557 B2 | 8/2011 | Soderlund |
| 8,014,847 B2 | 9/2011 | Shastri et al. |
| 8,027,518 B2 | 9/2011 | Baker et al. |
| 8,055,722 B2 | 11/2011 | Hille |
| 8,060,795 B2 | 11/2011 | Bakekolo et al. |
| 8,069,125 B2 | 11/2011 | Jung et al. |
| 8,079,054 B1 | 12/2011 | Dhawan et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,103,328 B2 | 1/2012 | Turner et al. |
| 8,135,606 B2 | 3/2012 | Dupree |
| 8,151,298 B2 | 4/2012 | Begeja et al. |
| 8,165,916 B2 | 4/2012 | Hoffberg et al. |
| 8,209,224 B2 | 6/2012 | Pradeep et al. |
| 8,229,469 B2 | 7/2012 | Zhang et al. |
| 8,235,725 B1 | 8/2012 | Hill |
| 8,239,030 B1 | 8/2012 | Hagedorn et al. |
| 8,255,267 B2 | 8/2012 | Breiter |
| 8,270,814 B2 | 9/2012 | Pradeep et al. |
| 8,296,172 B2 | 10/2012 | Marci et al. |
| 8,300,526 B2 | 10/2012 | Saito et al. |
| 8,326,002 B2 | 12/2012 | Hill |
| 8,327,395 B2 | 12/2012 | Lee et al. |
| 8,332,883 B2 | 12/2012 | Lee et al. |
| 8,335,715 B2 | 12/2012 | Pradeep et al. |
| 8,381,244 B2 | 2/2013 | King et al. |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,442,429 B2 | 5/2013 | Hawit |
| 8,467,133 B2 | 6/2013 | Miller |
| 8,473,345 B2 | 6/2013 | Pradeep et al. |
| 8,477,425 B2 | 7/2013 | Border et al. |
| 8,484,801 B2 | 7/2013 | Li et al. |
| 8,494,610 B2 | 7/2013 | Pradeep et al. |
| 8,494,905 B2 | 7/2013 | Pradeep et al. |
| 8,533,042 B2 | 9/2013 | Pradeep et al. |
| 8,600,100 B2 | 12/2013 | Hill |
| 8,635,105 B2 | 1/2014 | Pradeep et al. |
| 8,655,437 B2 | 2/2014 | Pradeep et al. |
| 8,684,742 B2 | 4/2014 | Siefert |
| 8,788,372 B2 | 7/2014 | Kettner et al. |
| 8,793,715 B1 | 7/2014 | Weitzenfeld et al. |
| 9,021,515 B2 | 4/2015 | Lee et al. |
| 2001/0013009 A1 | 8/2001 | Greening et al. .............. 705/10 |
| 2001/0020236 A1 | 9/2001 | Cannon |
| 2001/0029468 A1 | 10/2001 | Yamaguchi et al. |
| 2001/0032140 A1 | 10/2001 | Hoffman |
| 2001/0056225 A1 | 12/2001 | DeVito |
| 2002/0056087 A1 | 5/2002 | Berezowski et al. |
| 2002/0056124 A1 | 5/2002 | Hay |
| 2002/0059577 A1 | 5/2002 | Lu et al. .............. 725/9 |
| 2002/0065826 A1 | 5/2002 | Bell et al. |
| 2002/0072952 A1 | 6/2002 | Hamzy et al. |
| 2002/0077534 A1 | 6/2002 | DuRousseau |
| 2002/0103429 A1 | 8/2002 | deCharms |
| 2002/0111796 A1 | 8/2002 | Nemoto |
| 2002/0143627 A1 | 10/2002 | Barsade et al. |
| 2002/0155878 A1 | 10/2002 | Lert, Jr. et al. |
| 2002/0156842 A1 | 10/2002 | Signes et al. |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1 | 1/2003 | Gevins et al. |
| 2003/0036955 A1 | 2/2003 | Tanaka et al. |
| 2003/0037333 A1 | 2/2003 | Ghashghai et al. |
| 2003/0059750 A1 | 3/2003 | Bindler et al. |
| 2003/0063222 A1 | 4/2003 | Creed et al. .............. 348/687 |
| 2003/0065524 A1 | 4/2003 | Giacchetti et al. |
| 2003/0073921 A1 | 4/2003 | Sohmer et al. |
| 2003/0081834 A1 | 5/2003 | Philomin et al. |
| 2003/0093792 A1 | 5/2003 | Labeeb et al. .............. 725/46 |
| 2003/0100998 A2 | 5/2003 | Brunner et al. |
| 2003/0104865 A1 | 6/2003 | Itkis et al. |
| 2003/0149344 A1 | 8/2003 | Nizan .............. 600/300 |
| 2003/0165270 A1 | 9/2003 | Endrikhovski et al. |
| 2003/0177488 A1 | 9/2003 | Smith et al. |
| 2003/0208754 A1 | 11/2003 | Sridhar et al. |
| 2003/0233278 A1 | 12/2003 | Marshall |
| 2004/0001616 A1 | 1/2004 | Gutta et al. |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0073129 A1 | 4/2004 | Caldwell et al. |
| 2004/0092809 A1 | 5/2004 | DeCharms |
| 2004/0098298 A1 | 5/2004 | Yin |
| 2004/0101212 A1 | 5/2004 | Fedorovskaya et al. |
| 2004/0133081 A1 | 7/2004 | Teller et al. .............. 600/300 |
| 2004/0187167 A1 | 9/2004 | Maguire et al. |
| 2004/0193068 A1 | 9/2004 | Burton et al. |
| 2004/0210159 A1 | 10/2004 | Kibar |
| 2004/0219184 A1 | 11/2004 | Brown et al. .............. 424/423 |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0043646 A1 | 2/2005 | Viirre et al. |
| 2005/0060312 A1 | 3/2005 | Curtiss et al. .............. 707/7 |
| 2005/0062637 A1 | 3/2005 | El Zabadani et al. .............. 341/176 |
| 2005/0071462 A1 | 3/2005 | Bodin et al. .............. 709/224 |
| 2005/0071865 A1 | 3/2005 | Martins .............. 725/10 |

(56) References Cited

U.S. PATENT DOCUMENTS

| | | |
|---|---|---|
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0143629 A1 | 6/2005 | Farwell |
| 2005/0149964 A1 | 7/2005 | Thomas et al. |
| 2005/0154290 A1 | 7/2005 | Langleben |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0216243 A1 | 9/2005 | Graham et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0261980 A1 | 11/2005 | Hadi |
| 2005/0267798 A1 | 12/2005 | Panara |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0010470 A1 | 1/2006 | Kurosaki et al. |
| 2006/0035707 A1 | 2/2006 | Nguyen et al. |
| 2006/0041548 A1 | 2/2006 | Parsons et al. ................ 707/5 |
| 2006/0053110 A1 | 3/2006 | McDonald et al. |
| 2006/0093998 A1 | 5/2006 | Vertegaal |
| 2006/0111044 A1 | 5/2006 | Keller |
| 2006/0111644 A1 | 5/2006 | Guttag et al. |
| 2006/0129458 A1 | 6/2006 | Maggio |
| 2006/0149337 A1 | 7/2006 | John |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0176289 A1 | 8/2006 | Horn |
| 2006/0190822 A1 | 8/2006 | Basson et al. |
| 2006/0218046 A1 | 9/2006 | Carfi et al. |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0259371 A1 | 11/2006 | Perrier et al. |
| 2006/0293921 A1 | 12/2006 | McCarthy et al. |
| 2007/0016096 A1 | 1/2007 | McNabb |
| 2007/0038516 A1 | 2/2007 | Apple et al. ................ 705/14 |
| 2007/0048707 A1 | 3/2007 | Caamano et al. |
| 2007/0050256 A1 | 3/2007 | Walker et al. |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0112460 A1 | 5/2007 | Kiselik |
| 2007/0135727 A1 | 6/2007 | Virtanen et al. |
| 2007/0135728 A1 | 6/2007 | Snyder et al. |
| 2007/0136753 A1 | 6/2007 | Bovenschulte et al. |
| 2007/0150916 A1 | 6/2007 | Begole et al. |
| 2007/0214471 A1 | 9/2007 | Rosenberg |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0250846 A1 | 10/2007 | Swix et al. |
| 2007/0250901 A1 | 10/2007 | McIntire et al. ................ 725/146 |
| 2007/0265507 A1 | 11/2007 | de Lemos |
| 2007/0282566 A1 | 12/2007 | Whitlow et al. |
| 2007/0294132 A1 | 12/2007 | Zhang et al. |
| 2007/0294705 A1 | 12/2007 | Gopalakrishnan et al. |
| 2007/0294706 A1 | 12/2007 | Neuhauser et al. |
| 2008/0001600 A1 | 1/2008 | deCharms |
| 2008/0010110 A1 | 1/2008 | Neuhauser et al. |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091512 A1 | 4/2008 | Marci et al. ................ 705/10 |
| 2008/0097854 A1 | 4/2008 | Young |
| 2008/0109840 A1 | 5/2008 | Walter et al. |
| 2008/0125110 A1 | 5/2008 | Ritter |
| 2008/0147488 A1 | 6/2008 | Tunick et al. |
| 2008/0147742 A1 | 6/2008 | Allen ................ 707/104.1 |
| 2008/0152300 A1 | 6/2008 | Knee et al. |
| 2008/0162182 A1 | 7/2008 | Cazares et al. |
| 2008/0177197 A1 | 7/2008 | Lee et al. |
| 2008/0195471 A1 | 8/2008 | Dube et al. |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2008/0306398 A1 | 12/2008 | Uchiyama et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030780 A1 | 1/2009 | York et al. ................ 705/10 |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0069652 A1 | 3/2009 | Lee et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0082692 A1 | 3/2009 | Hale et al. |
| 2009/0083129 A1 | 3/2009 | Pradeep et al. |
| 2009/0088610 A1 | 4/2009 | Lee et al. |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0112077 A1 | 4/2009 | Nguyen et al. |
| 2009/0112117 A1 | 4/2009 | Rewari |
| 2009/0119154 A1 | 5/2009 | Jung et al. |
| 2009/0131764 A1 | 5/2009 | Lee et al. ................ 600/301 |
| 2009/0132441 A1 | 5/2009 | Muller et al. |
| 2009/0133047 A1 | 5/2009 | Lee et al. |
| 2009/0144780 A1 | 6/2009 | Toebes et al. |
| 2009/0150919 A1 | 6/2009 | Lee et al. |
| 2009/0150920 A1 | 6/2009 | Jones |

(56) References Cited

U.S. PATENT DOCUMENTS

| | | |
|---|---|---|
| 2009/0153328 A1 | 6/2009 | Otani et al. |
| 2009/0156907 A1 | 6/2009 | Jung et al. |
| 2009/0156955 A1 | 6/2009 | Jung et al. |
| 2009/0158308 A1 | 6/2009 | Weitzenfeld et al. |
| 2009/0163777 A1 | 6/2009 | Jung et al. |
| 2009/0164132 A1 | 6/2009 | Jung et al. |
| 2009/0171164 A1 | 7/2009 | Jung et al. |
| 2009/0187467 A1 | 7/2009 | Fang et al. |
| 2009/0195392 A1 | 8/2009 | Zalewski |
| 2009/0214060 A1 | 8/2009 | Chuang et al. |
| 2009/0221928 A1 | 9/2009 | Einav et al. |
| 2009/0248484 A1 | 10/2009 | Surendran et al. |
| 2009/0248496 A1 | 10/2009 | Hueter et al. |
| 2009/0248594 A1 | 10/2009 | Castleman et al. |
| 2009/0249223 A1 | 10/2009 | Barsook et al. |
| 2009/0253996 A1 | 10/2009 | Lee et al. |
| 2009/0259137 A1 | 10/2009 | Delic et al. |
| 2009/0271294 A1 | 10/2009 | Hadi |
| 2009/0287108 A1 | 11/2009 | Levy |
| 2009/0292587 A1 | 11/2009 | Fitzgerald |
| 2009/0300672 A1 | 12/2009 | Van Gulik |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0094702 A1 | 4/2010 | Silberstein |
| 2010/0121716 A1 | 5/2010 | Golan |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0153175 A1 | 6/2010 | Pearson et al. |
| 2010/0169153 A1 | 7/2010 | Hwacinski et al. |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0211439 A1 | 8/2010 | Marci et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0223094 A1 | 9/2010 | Cumming et al. |
| 2010/0234752 A1 | 9/2010 | Sullivan et al. |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250347 A1 | 9/2010 | Rainier et al. |
| 2010/0250458 A1 | 9/2010 | Ho |
| 2010/0257052 A1 | 10/2010 | Zito et al. |
| 2010/0263005 A1 | 10/2010 | White |
| 2010/0268540 A1 | 10/2010 | Arshi et al. |
| 2010/0268573 A1 | 10/2010 | Jain et al. |
| 2010/0269127 A1 | 10/2010 | Krug |
| 2010/0274152 A1 | 10/2010 | McPeck et al. |
| 2010/0287152 A1 | 11/2010 | Hauser |
| 2010/0306030 A1 | 12/2010 | Mawani |
| 2010/0306120 A1 | 12/2010 | Ciptawilangga |
| 2010/0317988 A1 | 12/2010 | Terada et al. |
| 2010/0318507 A1 | 12/2010 | Grant et al. |
| 2010/0325660 A1 | 12/2010 | Holden |
| 2010/0331661 A1 | 12/2010 | Nakagawa |
| 2011/0004089 A1 | 1/2011 | Chou |
| 2011/0015503 A1 | 1/2011 | Joffe et al. |
| 2011/0022965 A1 | 1/2011 | Lawrence et al. |
| 2011/0040202 A1 | 2/2011 | Luo et al. |
| 2011/0043759 A1 | 2/2011 | Bushinsky |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047035 A1 | 2/2011 | Gidwani et al. |
| 2011/0047121 A1 | 2/2011 | Pradeep et al. |
| 2011/0059422 A1 | 3/2011 | Masaoka |
| 2011/0084795 A1 | 4/2011 | Fukuyori |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0131274 A1 | 6/2011 | Hille |
| 2011/0138326 A1 | 6/2011 | Roberts et al. |
| 2011/0144519 A1 | 6/2011 | Causevic |
| 2011/0153391 A1 | 6/2011 | Tenbrock |
| 2011/0153423 A1 | 6/2011 | Elvekrog et al. |
| 2011/0161163 A1 | 6/2011 | Carlson et al. |
| 2011/0161790 A1 | 6/2011 | Junior et al. |
| 2011/0191142 A1 | 8/2011 | Huang et al. |
| 2011/0208515 A1 | 8/2011 | Neuhauser |
| 2011/0224569 A1 | 9/2011 | Isenhart et al. |
| 2011/0237923 A1 | 9/2011 | Picht et al. |
| 2011/0237971 A1 | 9/2011 | Pradeep et al. |
| 2011/0246574 A1 | 10/2011 | Lento et al. |
| 2011/0248729 A2 | 10/2011 | Mueller et al. |
| 2011/0256520 A1 | 10/2011 | Siefert |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0319975 A1 | 12/2011 | Ho et al. |
| 2012/0002848 A1 | 1/2012 | Hill |
| 2012/0036004 A1 | 2/2012 | Pradeep et al. |
| 2012/0036005 A1 | 2/2012 | Pradeep et al. |
| 2012/0046993 A1 | 2/2012 | Hill |
| 2012/0054018 A1 | 3/2012 | Pradeep et al. |
| 2012/0072289 A1 | 3/2012 | Pradeep et al. |
| 2012/0089552 A1 | 4/2012 | Chang et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0239407 A1 | 9/2012 | Lynch et al. |
| 2012/0245978 A1 | 9/2012 | Jain et al. |
| 2012/0249797 A1 | 10/2012 | Haddick et al. |
| 2012/0254909 A1 | 10/2012 | Serdiuk |
| 2013/0046577 A1 | 2/2013 | Marci et al. |
| 2013/0060125 A1 | 3/2013 | Zeman et al. |
| 2013/0094722 A1 | 4/2013 | Hill |
| 2013/0185140 A1 | 7/2013 | Pradeep et al. |
| 2013/0185141 A1 | 7/2013 | Pradeep et al. |
| 2013/0185142 A1 | 7/2013 | Pradeep et al. |
| 2013/0185145 A1 | 7/2013 | Pradeep et al. |
| 2013/0268279 A1 | 10/2013 | Srinivasan et al. |
| 2013/0304540 A1 | 11/2013 | Pradeep et al. |
| 2013/0332259 A1 | 12/2013 | Pradeep et al. |
| 2014/0162225 A1 | 6/2014 | Hill |
| 2014/0350431 A1 | 11/2014 | Hagedorn |

FOREIGN PATENT DOCUMENTS

| | | |
|---|---|---|
| GB | 1374658 | 11/1974 |
| GB | 2221759 | 2/1990 |
| JP | 2001-147944 | 5/2001 |
| JP | 2005-51654 | 2/2005 |
| JP | 2005160805 | 6/2005 |
| JP | 2006-227994 | 8/2006 |
| JP | 2006305334 | 11/2006 |
| JP | 2006-6355 | 7/2007 |
| KR | 200422399 | 7/2006 |
| WO | 9518565 | 7/1995 |
| WO | 9717774 | 5/1997 |
| WO | 9740745 | 11/1997 |
| WO | 9741673 | 11/1997 |
| WO | 2100241 | 12/2002 |
| WO | 2102238 | 12/2002 |

(56) References Cited

FOREIGN PATENT DOCUMENTS

| | | |
|---|---|---|
| WO | 2004049225 | 6/2004 |
| WO | 2008030831 | 3/2008 |
| WO | 2008055078 | 5/2008 |
| WO | 2008064431 | 6/2008 |
| WO | 2008077178 | 7/2008 |
| WO | 2008109694 | 9/2008 |
| WO | 2008109699 | 9/2008 |
| WO | 2008121651 | 10/2008 |
| WO | 2008137579 | 11/2008 |
| WO | 2008137581 | 11/2008 |
| WO | 2008141340 | 11/2008 |
| WO | 2008154410 | 12/2008 |
| WO | 2009018374 | 2/2009 |
| WO | 2009052833 | 4/2009 |
| WO | 2011055291 | 5/2011 |
| WO | 2011056679 | 5/2011 |

OTHER PUBLICATIONS

Boltz, M.G., "The cognitive of film and musical soundtracks", *Memory & Cognition*, 32(7):1194-1205 (2004).
Christie et al., "Autonomic specificity of discrete emotion and dimensions of affective space: a multivariate approach", *Int'l J. Psychophysiol.*, 51:143-153 (2004).
Coombes et al., "Emotion and movement: Activation of defensive circuitry alters the magnitude of a sustained muscle contraction", *Neurosci. Lett.*, 396:192-196 (2006).
Cryer et al., "Pull the plug on stress", *Harv. Bus. Rev.*, 81(7):102-107 (2003).
Demaree et al., "Predicting facial valence to negative stimuli from resting RSA: Not a function of active emotion regulation", *Cognition and Emotion*, 20(2):161-176 (2006).
Ekman et al., "Autonomic Nervous System Activity Distinguishes among Emotions", *Science*, 221 (4616):1208-1210 (1983).
Elton, C., "Measuring emotion at the symphony", http://www.boston.com, pp. 1-3 (2006).
Goldberg, C., "Getting wired could help predict emotions", http://www.boston.com, pp. 1-4 (2005).
Gomez et al., "Respiratory responses associated with affective processing of film stimuli", Biol. Psychol., 68:223-235 (2005).
Hall, B.F., "A New Approach to Measuring Advertising Effectiveness", Article 1502a:1-17 (2001).
Hall, B.F., "Advertising as a Factor of production", *Admop*, pp. 30-32 (2003).
Hall, B.F., "Is cognitive processing the right dimension", *Admap*, pp. 37-39 (2003).
Hall, B.F., "On Measuring the Power Communications", *JAR*, pp. 1-11 (2004).
Hall, B.F., "Research and strategy: a fall from grace", *Admap*, pp. 2-4 (2003).
Hall, B.F., "Review of Casting for Big Ideas, by Andrew Jaffe", pp. 1-2 (2003).
Hall, B.F., "Why Advertisers Do It", pp. 1-5 (2003).
Hubert, et al., "Autonomic, neuroendocrine, and subjective responses to emotion-inducing film stimuli", Int'l J. Psychophysiol., 11:131-140 (1991).
Levenson et al., "Emotion and Autonomic Nervous System Activity in the Minangkabau of West Sumatra", *J. Personality Soc. Psychol.*, 62(6):972-988 (1992).
Marci et al., "The Effect of Emotional Distance on Pyschophysiologic Concordance and Perceived Empathy Between Patient and Interviewer", *Appl. Psychophysiol. Biofeedback*, 31:115-129 (2006).
McCraty et al., "Analysis of twenty-four hour heart rate variability in patients with panic disorder", Biol. Psychol., 56(2):131-150 (2001).
McCraty et al., "Electrophysiolocial Evidence of Intuition: Part I. The Surprising Role of the Heart", J. Altern. Complement, Med., 10(1):133-143 (2004).
McCraty et al., "Electrophysiological Evidence of Intuition: Part 2. A System-Wide Process?", J. Altern. Complemeent. Med., 10(2/0):325-336 (2004).
McCraty et al., "Impact of a Workplace Stress Reduction Program on Blood Pressure and Emotional Health in Hypertensive Employees", *J. Altern. Complement. Med.*, 9(3):355-369 (2003).
McCraty et al., "The Effects of Different Types of Music on Mood, Tension, and Mental Clarity", *Altern. Ther. Health Med.*, 4(1):75-84 (1998).
McCraty et al., "The Effects of Emotions on Ahort-Term Power Spectrum Analysis of Heart Rate Variability", *Am. J. Cardiol.*, 76(14):1089-1093 (1995).
McCraty et al., "The Impact of a New Emotional Self-Management Program on Stress, Emotions, Heart Rate Variability, DHEA and Cortisol", *Intergr, Physiol. Behav. Sci.*, 33(2):151-170 (1998).
McCraty et al., "The Impact of an Emotional Self-Management Skill Course on Psychosocial Functioning and Autonomic Recovery to Stress in Middle School Children", Integr. Physiol. Behav. Sel., 34(4):246-268 (1999).
Melillo, W., "Inside the consumer mind: What Neuroscience can tell us about marketing", http://www.answerstream.com, pp. 1-13 (2006).
Miller et al., "Influence of Specific Emotional States on Autonomic Reactivity and Pulmonary Function in Asthmatic Children", *J. Am. Acad. Child Adolescent Psychiatry*, 36(5):669-677 (1997).
Murphy et al., "The Heart Reinnervates After Transplantation", *Ann. Thorac. Surg.*, 69(6):1769-1781 (2000).
Ranti, D., "Adding Science to Gut Check", *The News & Observer*, pp. 1 (2005).
Rosenberg, K., "Emotional R.O.I.", *The Hub*, pp. 24-25 (2006).
Tiller et al., "Cardiac Coherence: A New, NonInvasive Measure of Autonomic Nervous System Order", *Altern. Ther. Health Med.*, 2(1):52-65 (1996).
"Topline: Emotional Response to Advertising", *MSW Research*, pp. 1-6 (2005).
Umetani et al., "Twenty-Four Hour Time Domain Heart Rate Variability and Heart Rate: Relations to Age and Gender Over Nine Decades", *J. Am. Coll. Cardiol.*, 31(3):593-601 (1998).
Von Leupoldt et al., "Emotions in a Body Plethysmograph", *J. Psychophysiol.*, 18(4):170-176 (2004).
Watching Ads is Real Science Research Companies Monitor Physiological Reactions to Commercials to Determine Their Effectiveness,: [3 Star Edition] Bruce Horovitz Los Angeles Times, Orlando Sentinel [Orlando, Fla] Sep. 1, 1991: D1, 2 pgs.
Wearable feedback systems for rehabilitation Sung, Michael; Marci, Carl; Pentland, Alex. Journal of NeuroEngineering and Rehabilitation 2 (2005), 2 pgs.
Kallman, H. Effect of Blank Time on Picture Recognition. The American Journal of Psychology, vol. 97, No. 3, Autumn, 1984, pp. 399-406 [retrieved on Nov. 3, 2011]. Retrieved from the Internet: <URL: http://www.jstor.org/pss/1422527>.
International Search Report dated Mar. 24, 2008 of International Patent Application No. PCT/US2007/019398.
International Search Report dated Nov. 9, 2010 of International Patent Application No. PCT/US2010/031375.
International Search Report dated Oct. 21, 2010 of International Patent Application No. PCT/US2010/029162.
International Search Report dated Nov. 22, 2011 of International Patent Application No. PCT/US2011/033050.
Non-Final Office Action dated Oct. 18, 2010 of related U.S. Appl. No. 11/850,650.
Final Office Action dated Jun. 8, 2011 of related U.S. Appl. No. 11/850,650.
Non-Final Office Action dated Dec. 13, 2011 of related U.S. Appl. No. 11/850,650.
Notice of Allowance dated Jul. 16, 2012 of related U.S. Appl. No. 11/850,650.
Non-Final Office Action dated Dec. 21, 2011 of related U.S. Appl. No. 12/749,376.
Final Office Action dated Oct. 4, 2012 of related U.S. Appl. No. 12/749,376.
Non-Final Office Action dated Apr. 1, 2013 of related U.S. Appl. No. 12/749,376.

(56) References Cited

OTHER PUBLICATIONS

Final Office Action dated Dec. 17, 2013 of related U.S. Appl. No. 12/749,376.
Non-Final Office Action dated Apr. 25, 2012 of related U.S. Appl. No. 12/426,259.
Final Office Action dated Dec. 19, 2012 of related U.S. Appl. No. 12/426,259.
Non-Final Office Action dated Feb. 21, 2013 of related U.S. Appl. No. 13/657,432.
Final Office Action dated Nov. 5, 2013 of related U.S. Appl. No. 13/657,432.
Non-Final Office Action dated Feb. 13, 2013 of related U.S. Appl. No. 13/089,752.
Notice of Allowance dated Oct. 24, 2013 of related U.S. Appl. No. 13/089,752.
Australian Office Action dated Mar. 26, 2012 or corresponding Australian Patent Application No. 2007293092.
European Office Action dated Nov. 11, 2011 of corresponding European Patent Application No. 10717912.9.
European Supplementary Search Report dated Mar. 1, 2013 of corresponding European Patent Application No. 10717912.9.
European Office Action dated Mar. 14, 2013 of corresponding European Patent Application No. 10717912.9.
European Office Action dated Nov. 29, 2011 of corresponding European Patent Application No. 10717932.7.
European Search Report dated Aug. 8, 2013 of corresponding European Patent Application No. 10717932.7.
European Supplementary Search Report dated Aug. 27, 2013 of corresponding European Patent Application No. 10717932.7.
Japanese Office Action dated Apr. 23, 2012 of corresponding Japanese Patent Application No. 2009-527401.
Canadian Office Action dated Jul. 24, 2014 of related Canadian Patent Application No. 2,662,632.
Aaker et al., "Warmth in Advertising: Measurement, Impact, and Sequence Effects," The Journal of Consumer Research, vol. 12, No. 4, pp. 365-381, (Mar. 1986), 18 pages.
Akam, et al., "Oscillations and Filtering Networks Support Flexible Routing of Information," Neuron, vol. 67, pp. 308-320, Elsevier, (Jul. 29, 2010), 13 pages.
Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.
Anonymous, "Functional Magnetic Resonance Imaging," retrieved online from Wikipedia, the Free Encyclopedia on Aug. 23, 2011, at http://en.wikipedia.org/w/index.php?title=Functional_magnetic_resonance_imaging&oldid=319601772, (Oct. 13, 2009), 8 pages.
Arousal in Sport, in Encyclopedia of Applied Psychology, vol. 1, p. 159, retrieved from Google Books, (Spielberger, ed., Elsevier Academic Press, 2004), 1 page.
Badre, et al. "Frontal Cortex and the Discovery of Abstract Action Rules," Neuron, vol. 66, pp. 315-326, Elsevier, (Apr. 29, 2010), 12 pages.
Bagozzi et al., "The Role of Emotions in Marketing," Journal of the Academy of Marketing Science, vol. 27, No. 2, pp. 184-206, Academy of Marketing Science (1999), 23 pages.
Barcelo, et al., "Prefrontal Modulation of Visual Processing in Humans," Nature Neuroscience, vol. 3, No. 4, Nature America, http//neurosci.nature.com, (Apr. 2000), 5 pages.
Belch et al., "Psychophysiological and Cognitive Responses to Sex in Advertising," Advances in Consumer Research, vol. 9, pp. 424-427, (1982), 6 pages.
Blakeslee, "If You Have a 'Buy Button' in Your Brain, What Pushes It?" The New York Times, www.nytimes.com, (Oct. 19, 2004), 3 pages.
Braeutigam, "Neuroeconomics-From Neural Systems to Economic Behaviour," Brain Research Bulletin, vol. 67, pp. 355-360, Elsevier, (2005), 6 pages.

Buschman, et al., "Serial, Covert Shifts of Attention during Visual Search are Reflected by the Frontal Eye Fields and Correlated with Population Oscillations," Neuron, vol. 63, pp. 386-396, Elsevier, (Aug. 13, 2009), 11 pages.
Buschman, et al., "Top-Down Versus Bottom-Up Control of Attention in the Prefrontal and Posterior Parietal Cortices," Science, vol. 315, www.sciencemag.org/cgi/content/full/315/5820/1860, American Association for the Advancement of Science, (2007), 4 pages.
Buzsaki, "Neural Syntax: Cell Assemblies, Synapsembles, and Readers," Neuron, vol. 68, Elsevier, (Nov. 4, 2010), 24 pages.
Canolty, et al., "High Gamma Power is Phase-Locked to Theta Oscillations in Human Neocortex," Science, vol. 313, www.sciencemag.org, (Sep. 15, 2006), 3 pages.
Canolty, et al., "The Functional Role of Cross-Frequency Coupling," Trends in Cognitive Sciences, Elsevier, (Nov. 2010) 11 pages.
Chang, et al., "Categorical Speech Representation in Human Superior Temporal Gyrus," Nature Neuroscience, doi: 10.1038/nn.2641, (Oct. 3, 2010), 6 pages.
Cheng, et al. "Gender Differences in the Mu Rhythm of the Human Mirror-Neuron System," PLos ONE, vol. 3, Issue 5, www.plosone.org, (May 2008), 7 pages.
Crawford et al., "Self-Generated Happy and Sad Emotions in Low and Highly Hypnotizable Persons During Waking and Hypnosis: Laterality and Regional EEG Activity Differences," International Journal of Psychophysiology, vol. 24, pp. 239-266, (Dec. 1996), 28 pages.
D'Esposito, "From Cognitive to Neural Models of Working Memory," Phil. Trans. R. Soc. B, doi: 10.1098/rstb.2007.2086, (Mar. 30, 2007), 12 pages.
Davidson, et al., "The Functional Neuroanatomy of Emotion and Affective Style," Trends in Cognitive Sciences, vol. 3, No. 1, (Jan. 1999), 11 pages.
Desmet, "Measuring Emotions: Development and Application of an Instrument to Measure Emotional Responses to Products," Funology: From Usability to Enjoyment, pp. 111-123, Kluwer Academic Publishers, (Blythe et al., eds., 2004), 13 pages.
Dien, et al., "Application of Repeated Measures ANOVA to High-Density ERP Datasets: A Review and Tutorial," in Event-Related Potentials: A Methods Handbook pp. 57-82, (Todd C. Handy, ed., 2005), 14 pages.
Edgar, et al., "Digital Filters in ERP Research," in Event-Related Potentials: A Methods Handbook pp. 85-113, (Todd C. Handy, ed., 2005), 15 pages.
EEG Protocols, "Protocols for EEG Recording," retrieved from the Internet on Aug. 23, 2011, http://www.q-metrx.com/EEGrecordingProtocols.pdf, (Nov. 13, 2007), 3 pages.
Engel, et al., "Dynamic Predictions: Oscillations and Synchrony in Top-down Processing," Nature Reviews: Neuroscience, vol. 2, pp. 704-716, Macmillian Magazines Ltd., (Oct. 2001), 13 pages.
Filler, "MR Neurography and Diffusion Tensor Imaging: Origins, History & Clinical Impact of the First 50,000 Cases with an Assessment of Efficacy and Utility in a Prospective 5,000 Patient Study Group," Institute for Nerve Medicine, (Nov. 7, 2008), 56 pages.
Flinker, et al, "Sub-Centimeter Language Organization in the Human Temporal Lobe," Brain and Language, Elsevier Inc., (2010), doi.org/10.1016/j.bandl.2010.09.009, 7 pages.
Fogelson, et al., "Prefrontal Cortex is Critical for Contextual Processing: Evidence from Brain Lesions," Brain: A Journal of Neurology, vol. 132, pp. 3002-3010, doi:10.1093/brain/awp230, (Aug. 27, 2009), 9 pages.
Friedman, et al., "Event-Related Potential (ERP) Studies of Memory Encoding and Retrieval: A Selective Review," Microscopy Research and Technique 51:6-28, Wiley-Liss, Inc. (2000), 23 pages.
Fries, "A Mechanism for Cognitive Dynamics: Neuronal Communication through Neuronal Coherence," TRENDS in Cognitive Sciences, vol. 9, No. 10, pp. 474-480, Elsevier B.V. www.sciencedirect.com, (Oct. 2005), 7 pages.
Fuster, "Cortex and Memory: Emergence of a New Paradigm," Journal of Cognitive Neuroscience, vol. 21, No. 11, pp. 2047-2072, Massachusetts Institute of Technology, (Nov. 2009), 26 pages.

(56) References Cited

OTHER PUBLICATIONS

Gaillard, "Problems and Paradigms in ERP Research," Biological Psychology, Elsevier Science Publisher B.V. (1988), 10 pages.
Gargiulo, et al., "A Mobile EEG System with Dry Electrodes," (Nov. 2008), 4 pages.
Gazzaley, et al., "Top-Down Enhancement and Suppression of the Magnitude and Speed of Neural Activity," Journal of Cognitive Neuroscience, vol. 17, No. 3, pp. 507-517, Massachusetts Institute of Technology, (2005), 11 pages.
Haq, "This is Your Brain on Advertising," BusinessWeek, Market Research, (Oct. 8, 2007), 4 pages.
Hartikainen, et al., Manuscript Draft of "Emotionally Arousing Stimuli Compete with Attention to Left Hemispace," NeuroReport, (Sep. 8, 2007), 26 pages.
Hazlett, et al., "Emotional Response to Television Commercials: Facial EMG vs. Self-Report," Journal of Advertising Research, (Apr. 1999), 17 pages.
Herrmann, et al., "Mechanisms of Human Attention: Event-Related Potentials and Oscillations," Neuroscience and Biobehavioral Reviews, vol. 25, pp. 465-476, Elsevier Science Ltd., www.elsvevier.com/locate/neubiorev, (2001), 12 pages.
Hopf, et al., "Neural Sources of Focused Attention in Visual Search," Cerebral Cortex, 10:1233-1241, Oxford University Press, (Dec. 2000), 9 pages.
Kay, et al., "Identifying Natural Images from Human Brain Activity," Nature, vol. 452, pp. 352-356, Nature Publishing Group, (Mar. 20, 2008), 5 pages.
Keren, et al., "Saccadic Spike Potentials in Gamma-Band EEG: Characterization, Detection and Suppression," NeuroImage, http://dx.doi:10.1016/j.neuroimage.2009.10.057, (Oct. 2009), 16 pages.
Kishiyama, et al., "Novelty Enhancements in Memory Are Dependent on Lateral Prefrontal Cortex," The Journal of Neuroscience, vol. 29, No. 25, pp. 8114-8118, Society for Neuroscience (Jun. 24, 2009), 5 pages.
Kishiyama, et al., "Socioeconomic Disparities Affect Prefrontal Function in Children," Journal of Cognitive Neuroscience, vol. 21, No. 6, pp. 1106-1115, Massachusetts Institute of Technology, (2008), 10 pages.
Knight, "Consciousness Unchained: Ethical Issues and the Vegetative and Minimally Conscious State," The American Journal of Bioethics, vol. 8, No. 9, pp. 1-2, http://dx.doi.org/10.1080/15265160802414524, (Sep. 1, 2008), 3 pages.
Knight, "Contribution of Human Hippocampal Region to Novelty Detection," Nature, vol. 383, www.nature.com, (Sep. 19, 1996), 4 pages.
Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.
Knight, et al., "Prefrontal Cortex Regulates Inhibition and Excitation in Distributed Neural Networks," Acta Psychologica, vol. 101, pp. 159-178, Elsevier (1999), 20 pages.
Lee, et al., "What is 'Neuromarketing'? A Discussion and Agenda for Future Research," International Journal of Psychophysiology, vol. 63, pp. 199-204, Elsevier (2007), 6 pages.
Lekakos, "Personalized Advertising Services Through Hybrid Recommendation Methods: The Case of Digital Interactive Television," Department of Informatics, Cyprus University, (2004), 11 pages.
Lewis, et al., "Market Researchers Make Increasing Use of Brain Imaging," ACNR, vol. 5, No. 3, pp. 36-37, (Jul./Aug. 2005), 2 pages.
Luck, et al., "The Speed of Visual Attention in Schizophrenia: Electrophysiological and Behavioral Evidence," Schizophrenia Research, pp. 174-195, Elsevier B.V. www.sciencedirect.com, (2006), 22 pages.
Lui, et al., "Marketing Strategies in Virtual Worlds," The Data Base for Advances in Information Systems, vol. 38, No. 4, pp. 77-80, (Nov. 2007), 4 pages.
Makeig, et al., "Dynamic Brain Sources of Visual Evoked Responses," Science, vol. 295, www.sciencemag.org, (Jan. 25, 2002), 5 pages.
Makeig, et al., "Mining Event-Related Brain Dynamics," TRENDS in Cognitive Sciences, vol. 8, No. 5, (May 2004), www.sciencedirect.com, 7 pages.
Miltner, et al., "Coherence of Gamma-Band EEG Activity as a Basis for Associative Learning," Nature, vol. 397, www.nature.com, (Feb. 4, 1999), 3 pages.
Moran, et al. "Peak Frequency in the Theta and Alpha Bands Correlates with Human Working Memory Capacity," frontiers in Human Neuroscience, vol. 4, Article 200, www.frontiersin.org, (Nov. 11, 2010), 12 pages.
Neurofocus—"Neuroscientific Analysis for Audience Engagement," accessed on Jan. 8, 2010 at http://web.archive.org/web/20080621114525/www.neurofocus.com/BrandImage.htm, (2008), 2 pages.
Nielsen, "Neuroinformatics in Functional Neuroimaging," Informatics and Mathematical Modeling, Technical University of Denmark, (Aug. 30, 2002), 241 pages.
Osborne, "Embedded Watermarking for Image Verification in Telemedicine," Thesis submitted for the degree of Doctor of Philosophy in Electrical and Electronic Engineering, University of Adelaide (2005), 219 pages.
Page, et al., "Cognitive Neuroscience, Marketing and Research," Congress 2006—Foresight—The Predictive Power of Research Conference Papers, ESOMAR Publications, (Sep. 17, 2006), 25 pages.
Paller, et al., "Validating Neural Correlates of Familiarity," TRENDS in Cognitive Sciences, vol. 11, No. 6, www.sciencedirect.com, (May 2, 2007), 8 pages.
Picton, et al., "Guidelines for Using Human Event-Related Potentials to Study Cognition: Recording Standards and Publication Criteria," Psychophysiology, pp. 127-152, Society for Psychophysiological Research, (2000), 26 pages.
Rizzolatti, et al., "The Mirror-Neuron System," Annu. Rev. Neurosci., vol. 27, pp. 169-192, (Mar. 5, 2004), 30 pages.
Ruchkin, et al., "Modality-Specific Processing Streams in Verbal Working Memory: Evidence from Spatio-Temporal Patterns of Brain Activity," Cognitive Brain Research, vol. 6, pp. 95-113, Elsevier, (1997), 19 pages.
Rugg, et al., "Event-Related Potentials and Recognition Memory," TRENDS in Cognitive Sciences, vol. 11, No. 6, www.sciencedirect.com, (May 3, 2007), 7 pages.
Rugg, et al., "The ERP and Cognitive Psychology: Conceptual Issues," (Sep. 1996), 7 pages.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Spencer, "Averaging, Detection, and Classification of Single-Trial ERPs," in Event-Related Potentials: A Methods Handbook, pp. 209-227, (Todd C. Handy, ed., 2005), 10 pages.
Srinivasan, "High-Resolution EEG: Theory and Practice," in Event-Related Potentials: A Methods Handbook, pp. 167-188, (Todd C. Handy, ed., 2005), 12 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Taheri, et al., "A Dry Electrode for EEG Recording," Electroencephalography and clinical Neurophysiology, pp. 376-383, Elsevier Science Ireland Ltd. (1994), 8 pages.
Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

(56) References Cited

OTHER PUBLICATIONS

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.
Voytek, et al., "Dynamic Neuroplasticity after Human Prefrontal Cortex Damage," Neuron 68, pp. 401-408, Elsevier Inc., (Nov. 4, 2010), 8 pages.
Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, (Nov. 2009) 12 pages.
Voytek, et al., "Prefrontal Cortex and Basal Ganglia Contributions to Visual Working Memory," PNAS Early Edition, www.pnas.org/cgi/doi/10.1073/pnas.1007277107, (Oct. 19, 2010), 6 pages.
Voytek, et al., "Shifts in Gamma Phase-Amplitude Coupling Frequency from Theta to Alpha over Posterior Cortex during Visual Task," Frontiers in Human Neuroscience, doi: 10.3389/fnhum.2010.00191, (Oct. 19, 2010), 9 pages.
Wang, "Neurophysiological and Computational Principles of Cortical Rhythms in Cognition," Physiol Rev 90: pp. 1195-1268, American Physiological Society, www.prv.org, (2010), 75 pages.
William, "Brain Signals to Control Movement of Computer Cursor," Blog article: Brain Signals to Control Movement of Computer Cursor, Artificial Intelligence, retrieved from the Internet on Aug. 17, 2011, http://whatisartificialintelligence.com/899/brain-signals-to-control-movement-of-computer-cursor/, (Feb. 17, 2010), 3 pages.
Woldorf, "Distortion of ERP Averages Due to Overlap from Temporally Adjacent ERPs: Analysis and Correction," Psychophysiology, Society for Psychophysiological Research, vol. 30, pp. 98-119, Cambridge University Press, (1993), 22 pages.
Woodman, et al., "Serial Deployment of Attention During Visual Search," Journal of Experimental Psychology: Human Perception and Performance, vol. 29, No. 1, pp. 121-138, American Physiological Association, Inc., (2003), 18 pages.
Yamaguchi, et al., "Rapid-Prefrontal—Hippocampal Habituation to Novel Events," Journal of Neuroscience, vol. 24, No. 23, pp. 5356-5363, Society for Neuroscience, (Apr. 29, 2004), 8 pages.
Yap, et al., "TIMER: Tensor Image Morphing for Elastic Registration," NeuroImage, vol. 47, pp. 549-563, (May 3, 2009), 15 pages.
Yuval-Greenberg, et al., "Transient Induced Gamma-Band Response in EEG as a Manifestation of Miniature Saccades," Neuron, vol. 58, pp. 429-441, Elsevier Inc., (May 8, 2008), 13 pages.
Ziegenfuss, "Neuromarketing: Advertising Ethical & Medical Technology," The Brownstone Journal, vol. XII, pp. 69-73, Boston University, (May 2005), 9 pages.
Zyga, "A Baseball Cap That ReadsYour Mind," PhysOrg.com, located at www.physorg.com/news130152277.html, (May 16, 2008), 11 pages.
Ambler, et al., "Ads on the Brain; A Neuro-Imaging Comparison of Cognitive and Affective Advertising Stimuli," London Business School, Centre for Marketing Working Paper, No. 00-902, (Mar. 2000), 23 pages.
Clifford, "Billboards That Look Back," The New York Times, NYTimes.com, available at http://www.nytimes.com/2008/05/31/business/media/31billboard.html, (May 31, 2008), 4 pages.
Meriam-Webster Online Dictionary, Definition of "Tangible," available at http://www.meriam-webster.com/dictionary/tangible, 1 page.
Mosby's Dictionary of Medicine, Nursing, & Health Professions, 2009, Mosby, Inc., Definition of "Alpha Wave," 1 page.
Mosby's Dictionary of Medicine, Nursing, & Health Professions, 2009, Mosby, Inc., Definition of "Beta Wave," 1 page.
Sapien Systems, "User Monitoring," Interfacing with Intelligence, available at http://web.archive.org/web/20030818043339/http://www.sapiensystems.com/eyetracking.html, (Aug. 18, 2003), 1 page.
Bimler, et al., "Categorical Perception of Facial Expressions of Emotion: Evidence from Multidimensional Scaling," Cognition and Emotion, vol. 15, No. 5, pp. 633-658, (Sep. 2001), 26 pages.
De Gelder et al., "Categorical Perception of Facial Expressions: Categories and their Internal Structure," Cognition and Emotion, vol. 11, No. 1, pp. 1-23, (1997), 23 pages.
Griss, et al., "Characterization of Micromachined Spiked Biopotential Electrodes", Biomedical Engineering, IEEE Transactions, vol. 49, No. 6, (Jun. 2002), 8 pages.
Meriam Webster Online Dictionary, Definition of "Virtual Reality," available at http://www.meriam-webster.com/dictionary/virtual%20reality, 2 pages.
Newell, et al., "Categorical Perception of Familiar Objects," Cognition, vol. 85, No. 2, pp. 113-143, Elsevier Science B.V., (Sep. 2002), 31 pages.
Padgett, et al., "Categorical Perception in Facial Emotion Classification," In Proceedings of the 18th Annual Conference of the Cognitive Science Society, pp. 249-253, (1996), 5 pages.
Sullivan, et al., "A Brain-Machine Interface Using Dry-Contact, Low-Noise EEG Sensors," In Proceedings of the 2008 IEEE International Symposium on Circuits and Systems, (May 18, 2008), 4 pages.
Allen, et al., "A Method of Removing Imaging Artifact from Continuous EEG Recorded during Functional MRI," NeuroImage, vol. 12, pp. 230-239, Academic Press, (Aug. 2000), 12 pages.
Barreto, et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Jung, et al., "Analysis and Visualization of Single-Trial Event-Related Potentials," Human Brain Mapping, vol. 14, pp. 166-185, Wiley-Liss, Inc., (2001), 20 pages.
Klimesch, "EEG Alpha and Theta Oscillations Reflect Cognitive and Memory Performance: A Review and Analysis," Brain Research Reviews, vol. 29, pp. 169-195, Elsevier Science B.V., (1999), 27 pages.
Krakow, et al., "Methodology: EEG-Correlated fMRI," Functional Imaging in the Epilepsies, Lippincott Williams & Wilkins, (2000), 17 pages.
Krugman, "Brain Wave Measures of Media Involvement," Journal of Advertising Research vol. 11, No. 1, pp. 3-9, The British Library, (Feb. 1971), 7 pages.
The Mathworks, Inc., "MATLAB: The Language of Technical Computing," Data Analysis, Version 7, pp. 4-19, (2005), 3 pages.
Oberman, et al., "EEG Evidence for Mirror Neuron Activity During the Observation of Human and Robot Actions Toward an Analysis of the Human Qualities of Interactive Robots," Neurocomputing, vol. 70, pp. 2194-2203, Elsevier Science B.V., (2007), 10 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.
Palva, et al., "Phase Synchrony Among Neuronal Oscillations in the Human Cortex," Journal of Neuroscience, vol. 25, No. 15, pp. 3962-3972, Society for Neuroscience, (2005), 11 pages.
Lachaux, et al., "Measuring Phase Synchrony in Brain Signals," Human Brain Mapping, vol. 8, pp. 194-208, Wiley-Liss, Inc., (1999) 15 pages.
Merriam-Webster Online Dictionary, Definition for "Resonance," available at http://www.merriam-webster.com/dictionary/resonance, 4 pages.
Enghoff, Thesis: "Moving ICA and Time-Frequency Analysis in Event-Related EEG Studies of Selective Attention," Technical University of Denmark, (Dec. 1999), 54 pages.
Zhang, "Will You Use Animation on Your Web Pages?" Doing Business on the Internet: Opportunities and Pitfalls, C. Romm and F. Sudweeks (eds.), Spring-Verlag, (1999), 17 pages.
Coan, et al., "Voluntary Facial Expression and Hemispheric Asymmetry Over the Frontal Cortex," Psycophysiology, vol. 38, pp. 912-924, Cambridge University Press, (Nov. 2001), 14 pages.

(56) References Cited

OTHER PUBLICATIONS

Duchowski, "A Breadth-First Survey of Eye-tracking Applications," Beahavior Research Methods, Instruments, and Computers, vol. 34, No. 4, pp. 455-470, Psychonomic Society, Inc., (Nov. 2002), 16 pages.

Heo, et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.

Rothschild, et al., "Predicting Memory for Components of TV Commercials from EEG," Journal of Consumer Research, vol. 16, No. 4, pp. 472-478, University of Chicago Press, (Mar. 1990), 8 pages.

Beaver, John D., et al., "Individual Differences in Reward Drive Predict Neural Responses to Images of Food", Journal of Neuroscience, vol. 26, No. 19, pp. 5160-5166, Society for Neuroscience, (May 10, 2006), 7 pages.

Tapert, et al., "Neural Response to Alcohol Stimuli in Adolescents With Alcohol Use Disorder", Arch Gen Psychiatry, vol. 60, pp. 727-735, American Medical Association, (Jul. 2003), 9 pages.

Shandlen, et al., "A Computational Analysis of the Relationship between Neuronal and Behavioral Responses to Visual Motion", Journal of Neuroscience, vol. 16, No. 4, pp. 1486-1510, Society for Neuroscience, (Feb. 15, 1996), 25 pages.

Cassanello, et al., "Neuronal Responses to Moving Targets in Monkey Frontal Eye Fields", Journal of Neurophysiology, pp. 1544-1556, American Psychological Society, (Sep. 2008), 16 pages.

Axis Communications, "Improve Your Merchandising Effectiveness. Get the Full Picture with Network Video" (2008), available at :http://www.axis.com/files/user_scenarios/ap_ret_merchandising_31107_en_0803_1o.pdf, 2 pages.

Millwardbrown, "Should My Advertising Stimulate an Emotional Response?" (2009) available at http://www.wpp.com/~/media/sharedwpp/readingroom/marketing/millward_brown_emotional_response.pdf, 6 pages.

Mehta, et al., "Reconsidering Recall and Emotion in Advertising", Journal of Advertising Research, pp. 49-56, (Mar. 2006), 9 pages.

Cheung, et al., "Mining Customer Product Ratings for Personalized Marketing," Decision Support Systems, vol. 35, pp. 231-243, Elsevier Science B.V., (2003), 13 pages.

Darrow, "Psychological and Psychophysiological Significance of the Electroencephalogram," Psychological Review, pp. 157-168, Institute for Juvenile Research, Chicago, (May 1947), 12 pages.

Stamm, "On the Relationship between Reaction Time to Light and Latency of Blocking the Alpha Rhythm," Electroencephalography and Clinical Neurophysiology, pp. 61-68, (Feb. 1952), 8 pages.

Mizuki, et al., "Periodic Appearance of Theta Rhythm in the Frontal Midline Area During Performance of a Mental Task,:" Electroencephalography and Clinical Neurophysiology, vol. 49, pp. 345-351, Elsevier/North-Holland Scientific Publishers, Ltd., (Aug. 1980), 7 pages.

Ekman, et al., Measuring Facial Movement, Environmental Psychology and Nonverbal Behavior, vol. 1, No. 1, pp. 56-75, (Fall 1976), 20 pages.

Ekman, et al., *Facial Action Coding System: A Technique for Measurement of Facial Movement*, Consulting Psychologists Press, Palo Alto, Calif. (1978).

Ekman, et al., *Unmasking the Face—A Guide to Recognizing Emotions from Facial Clues*, Prentice-Hall, Inc., Englewood Cliffs, N.J. (1979).

Ekman, et al., "Facial Signs of Emotional Experience", Journal of Personality & Social Psychology, vol. 39, No. 6, pp. 1125-1134, American Psychological Association, Inc., (Dec. 1980), 10 pages.

Izard, *The Maximally Discriminative Facial Movement Coding System*, (Rev. ed.), Instructional Resources Center, University of Delaware, Newark, Del. (1983).

Izard, C., Dougherty, L., Hembree, E., *A System for Identifying Affect Expressions by Holistic Judgments (AFFEX)*, Instructional Resources Center, University of Delaware, Newark, Del. (1983).

Jia, et al., "Extending the Feature Set for Automatic Face Recognition," International Conference on Image Processing and Its Applications, pp. 155-158, University of Southaven, UK, (1992), 6 pages.

Lisetti, et al., "Using Noninvasive Wearable Computers to Recognize Human Emotions from Physiological Signals," EURASIP Journal of Applied Signal Processing, vol. 11, pp. 1672-1687, Hindawi Publishing Corporation, (Sep. 2004), 16 pages.

Jaimes, et al., "Multimodal Human-Computer Interaction: A Survey," Computer Vision and Image Understanding vol. 108, pp. 116-134, Elsevier, Inc., (Oct.-Nov. 2007), 19 pages.

McClure, et al., "Neural Correlates of Behavioral Preference for Culturally Familiar Drinks," Neuron, vol. 44, pp. 379-387, Cell Press, (Oct. 14, 2004), 9 pages.

Opitz, "Neuromarketing: An Introduction," PowerPoint Presentation (2008), available at http://www.powershow.com/view/94a7b-YzlmN/Neuromarketing_powerpoint_ppt_presentation (last accessed Oct. 14, 2015), 20 pages.

United States Patent and Trademark Office, "Non-Final Office Action," issued in connection with U.S. Appl. No. 12/749,376, mailed on Aug. 29, 2014, 18 pages.

United States Patent and Trademark Office, "Final Office Action," issued in connection with U.S. Appl. No. 12/749,376, mailed on Mar. 13, 2015, 20 pages.

United States Patent and Trademark Office, "Non-Final Office Action," issued in connection with U.S. Appl. No. 12/749,376, mailed on Jul. 5, 2015, 25 pages.

United States Patent and Trademark Office, "Final Office Action," issued in connection with U.S. Appl. No. 12/749,376, mailed on Oct. 23, 2015, 29 pages.

United States Patent and Trademark Office, "Non-Final Office Action," issued in connection with U.S. Appl. No. 12/426,259, mailed on Jan. 14, 2015, 37 pages.

United States Patent and Trademark Office, "Final Office Action," issued in connection with U.S. Appl. No. 12/426,259, mailed on Sep. 24, 2015, 38 pages.

United States Patent and Trademark Office, "Non-Final Office Action," issued in connection with U.S. Appl. No. 13/089752, mailed on Jul. 2, 2014, 31 pages.

United States Patent and Trademark Office, "Final Office Action," issued in connection with U.S. Appl. No. 12/426,259, mailed on Feb. 24, 2015, 21 pages.

Landau et al., "Different Effects of Voluntary and Involunatry Attention on EEG Activity in the Gamma Band," Journal of Neuroscience 27(44), Oct. 31, 2007, pp. 11986-11990, 5 pages.

United States Patent and Trademark Office, "Non-Final Office Action," issued in connection with U.S. Appl. No. 13/657,432, mailed on Jul. 2, 2014, 31 pages.

United States Patent and Trademark Office, "Final Office Action," issued in connection with U.S. Appl. No. 13/657,432, mailed on Feb. 24, 2015, 20 pages.

United States Patent and Trademark Office, "Notice of Allowance," issued in connection with U.S. Appl. No. 12/749,376, mailed on Jan. 29, 2016, 50 pages.

United States Patent and Trademark Office, "Notice of Allowance," issued in connection with U.S. Appl. No. 13/657,432, mailed on Apr. 25, 2016, 12 pages.

M. Corbetta et al., "Control of Goal-Directed and Stimulus-Driven Attention in the Brain," Nature Reviews Neuroscience, vol. 3, pp. 201-15 (Mar. 2002), 15 pp.

Becker, S. "A Study of Web Usability for Older Adults Seeking Online Health Resources," ACM Transactions on Computer-Human Interaction, vol. 11, No. 4, pp. 387-406 (Dec. 2004), 20 pages.

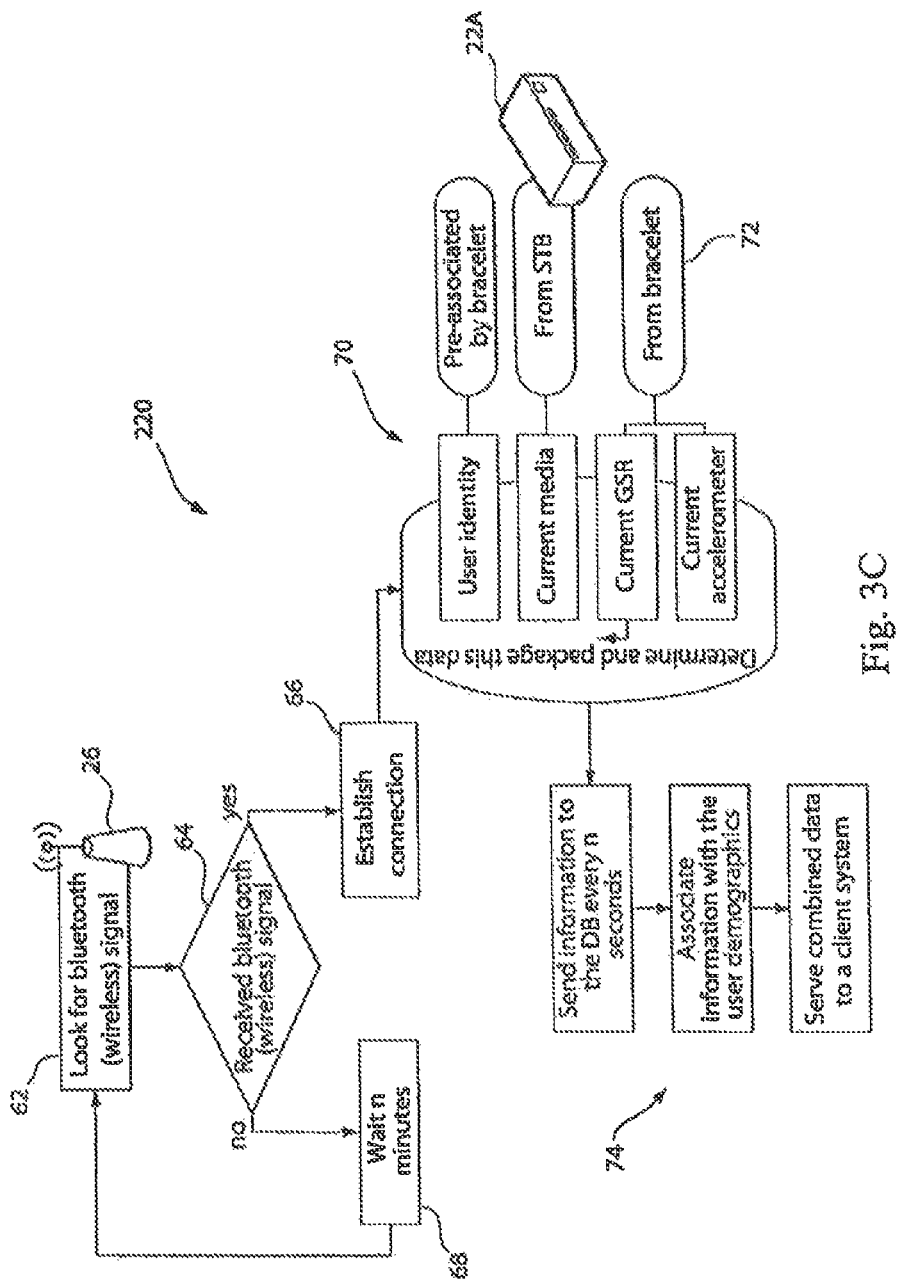

SHORT IMAGERY TASK (SIT) RESEARCH METHOD

CROSS-REFERENCE TO RELATED APPLICATIONS

This patent is a continuation of U.S. Pat. No. 8,684,342, filed Apr. 19, 2011, which claims priority under 35 U.S.C. §119 to U.S. Provisional Patent Application No. 61/325,794, filed Apr. 19, 2010, which is incorporated by reference in its entirety herein.

FIELD OF THE INVENTION

The present invention relates to biologically and behaviorally based methods of measuring audience response to a short stimulus.

BACKGROUND OF THE INVENTION

There are many different kinds of audio, visual and audio-visual presentations and activities that people are exposed to every day. These presentations serve as sensory experiences that stimulate our senses and are known to result in biologically based responses that can be measured electronically and mechanically (for example, heart rate, respiration rate, blood pressure, and skin conductance).

A commonly used approach in making measurements for evaluating these presentations is that of interrogation, wherein the television/media viewer and/or Internet user and/or game player is asked to identify himself or herself as a member of the television/media audience or as an Internet user or as a game player. In connection with television viewing, this inquiry is usually done by means of an electronic prompting and data input device (for example, as in a Portable People Meter by Arbitron, Inc.) associated with a monitored receiver in a statistically selected population and monitoring site. The member identification may also include age, sex, and other demographic data. It is common to store both the demographic data and the tuning data associated with each monitored receiver in the statistically selected monitoring site in store-and-forward equipment located within the monitoring site and to subsequently forward these data to a central office computer via a direct call over the public switched telephone network, or via the Internet, on a regular basis. However, these non-biologically based self-report methods of measuring audience response are known to be highly error prone.

In fact, personal logs are subjective resulting in recall biases, home monitoring devices require event-recording by the person and suffer low compliance, while digital monitoring of cable and internet signals cannot identify which household member or members are in the audience nor can they evaluate the level of responsiveness by those members. Other methods of self-report offer valuable data, but are highly error prone and cannot track the moment-to moment responses to media consumption and participation in interactive activities.

In particular, with the development of the internet and its expansion into many everyday activities, people are constantly exposed to interactive media and activities. Nonetheless, the ability to measure and evaluate the user experience, effectiveness, and the usability of these interactive media has been limited. In fact, current methodologies for measuring or evaluating user experience, effectiveness, and usability of websites and other interactive internet and software media has thus far been limited to traditional self-report and eye-tracking on an individual user basis. These prior art techniques involved asking the individual user questions about the experience and evaluating where the user was looking during the interactive activity. Some companies (e.g., NeuroFocus, EmSense) also incorporate EEG in the process and some companies propose to measure cognitive activity (e.g., Eye Tracking, Inc.) from pupillary responses. These companies use these measures in attempts to determine emotional states, such as happiness and to study the effects on implicit memory.

With previous methods known in the art used to analyze responses to still images, phrases, sounds, words or brief productions (i.e., <15 seconds), individuals typically utilize self-report methods or alternatively methods exclusively. These earlier testing methods relied on examining physiological responses in each individual channel; however, to date, no method exists that combines multiple physiological response and self-report responses to calculate a single score that is predictive for a population. Thus, a need in the art exists for a method that is capable of integrating self-report and physiological data and capable of integrating data across multiple physiological channels into a single score.

SUMMARY OF THE INVENTION

The present invention is directed to a method of determining a measure of response of an audience to a target stimulus including:

providing a biometric sensor device operable to measure at least a first biometric parameter and a second biometric parameter;

providing each participant an eye tracking device;

exposing each participant of the audience to a presentation over a period of time wherein the presentation includes a first series of standardized stimuli, at least one target stimulus, and a second series of standardized stimuli and wherein each participant is exposed to a null exposure following exposure to each stimulus;

providing a computer system operable to receive data representative of the at least two biometric parameters, wherein the computer further includes a memory for storing the data;

re-exposing each participant to the at least one target stimulus;

providing each participant at least one self-report question;

calculating a single physiological score for each participant based on the data collected on the at least two biometric parameters;

calculating an Emotional Impact Score for the audience using each participant's single physiological score; and calculating an Explicit Emotion Score.

In one embodiment, the first series of standardized stimuli includes between 4 and 20 standardized images and the second series of standardized stimuli includes between 4 and 20 standardized images. In another embodiment, the biometric sensor device is operable to measure at least a third biometric parameter. In yet another embodiment, the method further includes plotting the Emotional Impact Score and the Explicit Emotion Score for the audience on a biphasic graph.

The present invention also relates to a method of determining a measure of response of an audience to a target stimulus including:

providing each participant a biometric sensor device capable of measuring at least two biometric parameters;

providing each participant an eye tracking device;

exposing each participant to a series of standardized stimuli, wherein each standardized image is followed by a null exposure;

exposing each participant to a first target stimulus, wherein the target stimulus is followed by a null exposure;

exposing each participant to a series of standardized stimuli, wherein each standardized image is followed by a null exposure;

measuring at least two biometric parameters during each exposure;

providing a computer system connected to the biometric sensor operable to receive data representative of the at least two biometric parameters and operable to integrate the data across channels into a single physiological score;

re-exposing each participant to each target stimulus;

providing each participant at least one self-report question;

calculating a single physiological score for each participant based on the data collected on the at least two biometric parameters;

calculating an Emotional Impact Score for the audience using each participant's single physiological score; and calculating an Explicit Emotion Score.

In one embodiment, the audience includes at least 10 participants. In another embodiment, the method further includes a Top of the Mind Task. In yet another embodiment, the method further includes plotting the Emotional Impact Score and the Explicit Emotion Score for the audience on a biphasic graph.

The present invention is also directed to a method of determining a measure of response of an audience to a target stimulus including:

providing a first biometric sensor device operable to measure at least one biometric parameter;

providing a second biometric sensor device operable to measure at least two biometric parameters;

providing each participant an eye tracking device operable to determine one or more gaze locations over a presentation where at least one participant is looking;

exposing each participant of the audience to a presentation over a period of time wherein the presentation includes a first series of standardized stimuli, at least one target stimulus, and a second series of standardized stimuli and wherein each participant is exposed to a null exposure for a period of time following exposure to each stimulus;

providing a computer system operable to receive data representative of the at least two biometric parameters, wherein the computer further includes a memory for storing the data;

re-exposing each participant to the at least one target stimulus;

providing each participant at least one self-report question;

calculating a single physiological score for each participant based on the data collected on the at least two biometric parameters;

calculating an Emotional Impact Score for the audience using each participant's single physiological score; and calculating an Explicit Emotion Score for the audience using each participant's response to the at least one self-report question.

In one embodiment, the method further includes plotting the Emotional Impact Score and the Explicit Emotion Score for the audience on a biphasic graph. In another embodiment, the participant is provided at least three self-repost questions. In yet another embodiment, each participant is exposed to the standardized stimuli and the at least one target stimulus for between about 5 seconds and about 20 seconds, and wherein each participant is exposed to a null exposure for between about 5 seconds and about 15 seconds. In still another embodiment, the method further includes providing each participant with at least three self-repose questions and calculating an Explicit Emotion Score for the audience using each participant's response to the at least three self-report questions.

BRIEF DESCRIPTION OF THE DRAWINGS

Further features and advantages of the invention can be ascertained from the following detailed description that is provided in connection with the drawings described below:

FIG. 3C is a flow diagram of one aspect of the in-home system embodiment, its ability to identify who in a given household is actually experiencing media;

DETAILED DESCRIPTION OF THE PREFERRED EMBODIMENTS

The present invention is directed to a short imagery task (SIT) research method and system for measuring an audience's biometric (physical, behavioral, biological and self-report) responses to a sensory stimulus and determining a measure of the audience's engagement to the sensory stimulus. In particular, the invention is directed to a method and system for measuring one or more biometric responses of one or more persons being exposed to a sensory stimulus, presentation or interactive activity for brief periods of time. Furthermore, the invention can be used to determine whether the presentation or interactive activity is more effective in a population relative to other presentations and other populations (such as may be defined by demographic or psychographic criterion) and to help identify elements of the presentation that contribute to the high level of engagement and the effectiveness and success of the presentation.

There are many different kinds of audio, visual, and audio-visual presentations that people are exposed to every day. These presentations serve as stimuli to our senses. Many of these presentations are designed to elicit specific types of responses. In some instances, an artist, musician, or movie director has created a presentation that is intended to elicit one or more emotions or a series of responses from an audience. In other instances, the presentation is intended to educate or promote a product, a service, an organization, or a cause. There are also applications where the audience is exposed to or interacts with one or more live persons such as during a focus group, during an interview situation, or any such social interaction. The audience can also be presented with an interactive activity or task that can include one or more audio, visual and audio-visual presentations and allows the audience to interact with a computer, an object, a situation, an environment, or another person to complete an activity or task. Additionally, the participants or audience may be asked to hold or physically manipulate an object. For example, the participants may be asked to handle a product.

These sensory stimuli can be in the form of a sound or a collection of sounds, a single picture or collection of pictures or an audio-visual presentation that is presented passively such as on television or radio, or presented in an interactive environment such as in a video game, live interaction or internet experience. The sensory stimuli can be pre-recorded or presented live such as in a theatrical performance or legal proceeding (passive) or a real-world situation (virtual reality or simulation) such as participating on a boat cruise, focus group, online activity, board game, computer game, or theme park ride (interactive).

Figure 1:
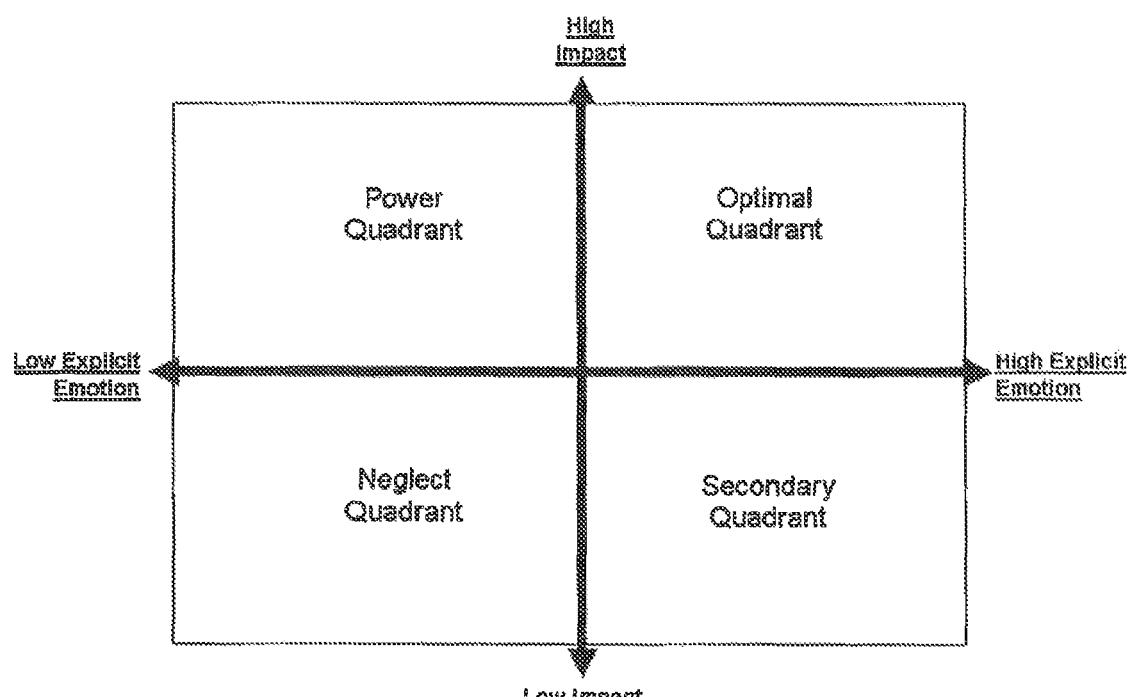
FIG. 1 is an example of a biphasic graph.

The SIT method of the present invention combines a mixture of biometric measures (specifically skin conductance, heart rate, respiratory rate, and pupil dilation) with a self-report technique in order to assess stimuli displayed for brief periods of time and ranking along two dimensions. The dimensions are referred to as Emotional Impact and Explicit emotion. The present invention is directed to methods for obtaining these scores and utilizing them for market research purposes. Another aspect of this invention involves generating graphs for stimuli using a bi-dimensional graph or biphasic graph, as shown in FIG. 1, based on the information collected according to the SIT method. Using the SIT method and biphasic graphs, marketers can make decisions on which stimuli to utilize and how to utilize stimuli in marketing executions by understanding how people respond to them physiologically and consciously.

Responses that are based in human biology can have multiple physiologic and behavioral correlations. One aspect of the invention includes collecting at least one measurement by tracking a participant's eyes. The eye-tracking measures can include, but are not limited to, visual attention as estimated by gaze location, fixation duration, and movement within a localized area. Another aspect of the present invention includes collecting biometric measurements from the participants. Biometric measures may include, but are not limited to, pupillary responses, skin conductivity, heart rate, heart rate variability, brain-wave activity and respiration activity. A third aspect of the present invention includes collecting behavioral data from the participants. Behavioral type biometric responses can include, but are not limited to, facial micro and macro-expressions, head tilt, head lean, body position, body posture, body movement, and amount of pressure applied to a computer mouse or similar input or controlling device. Self-report type biometric measures can include, but are not limited to, survey responses to items such as perception of the experience, perception of usability or likeability of experience, level of personal relevance to user, attitude toward content or advertising embedded in the content, intent to purchase product, game or service, and changes in responses from before and after or pre-post testing.

In one aspect of the present invention, the data plotted on a biphasic graph is analyzed according to a prototypical quadrant interpretation. In an embodiment of the invention, a prototypical quadrant interpretation includes labeling the upper right quadrant as the optimal quadrant, the lower right quadrant as the secondary quadrant, the upper left quadrant as the power quadrant, and the lower left quadrant as the neglect quadrant. The SIT method of the present invention can be used to plot data for a target stimulus in one of these quadrants. An investigator or consultant can then provide descriptive analyses based on the quantitative data for each target stimulus. For example, if the Emotional Impact Score and the Explicit Emotion Score result in a value that is plotted in the upper right quadrant of the biphasic graph shown in FIG. 1, then the stimulus falls within the optimal quadrant.

In an embodiment of the present invention, concepts with scores that fall within the optimal quadrant may be described as having good stopping power, able to generate unconscious and conscious emotional response and learning, and able to activate approach emotions. These concepts may also be described as effective in a wide variety of settings.

Similarly, concepts with scores that fall within the secondary quadrant may be described as lacking stopping power, able to generate less of an unconscious response, but able to activate approach emotions. These concepts may also be effective when paired with more attention pulling stimuli or placed in a context that draws attention to them.

Concepts with scores that fall within the power quadrant may be described as having good stopping power and able to activate an immediate unconscious response. However, these concepts also can activate withdrawal emotions. These concepts may be effective when used to garner attention, activate need states, and when placed in a context that involves them in a larger context (i.e., with other concepts or text) designed to create approach emotions. It may be preferable to use these concepts sparingly.

Concepts with scores that fall within the neglect quadrant may be described as lacking stopping power, incapable of generating an unconscious response, and rarely able to activate approach emotions. These concepts may also have questionable utility based on their inability to generate an impact either consciously or unconsciously, and they may also be easily ignored.

In some embodiments of the present invention, it may be preferable to modify the standard or base quadrant interpretations according to the specific study questions, the specific study stimuli, and the plan for using the stimuli.

The present invention embodies a research method that allows investigators to assess rapid reactions and conscious reactions to stimuli. The method describes a process for calculating an Emotional Impact Score and an Explicit Emotion Score to create charts and to plot biphasic graphs. Investigators can utilize this information by providing it to third parties or to act as consultants. In one aspect of the invention, the information provided by the method is used to achieve various marketing objectives. In another aspect of the invention, the information provided by the method is used to evaluate any type of stimulus.

In an embodiment of the present invention, the data collection method entails at least a three-step process. The first step of the process entails collecting information for use in calculating an Emotional Impact Score. The second step of the process entails collecting data for use in calculating an Explicit Emotion Score. Finally, the raw data are used to calculate an Emotional Impact Score and an Explicit Emotion Score, both of which are used to plot a stimulus on a biphasic graph. It should be understood that additional data may be collected in addition to the information required for calculating the Emotional Impact Score and the Explicit Emotion Score. For example, in a further embodiment of the present invention, gaze locations are collected for a sample population. As will be discussed in more detail below, gaze locations may be used to generate biometric emotive and biometric cognitive maps.

Emotional Impact Score

The Emotional Impact Score is calculated using reference to a database. The Emotional Impact Score is a measure of how a target stimulus fits within a database distribution with regard to its standardized distance from the database mean using the database standard deviation. Thus, the Emotional Impact Score for a given stimulus compares the reaction of a population sample to standardized reactions of database representative of a larger population.

To collect information for calculating the Emotional Impact Score of the present invention, individuals in a sample population complete a task separately after providing consent to participate in testing. The general testing procedure includes at least one baseline exposure or exposure to a standardized media immediately followed by a null exposure, for example a blank screen or silence. After establishing the baseline parameters for measurement through exposure to standardized media, the participants are then exposed to at least one target stimulus, which is immediately followed by a null exposure. Once a participant views all of the target stimuli in the task, the participant views a second series of standardized exposures, each being separated by a null exposure.

In another aspect of the invention, following consent, each participant is outfitted with a system capable of detecting multiple biometric measures, such as the Innerscope® Biometric Monitoring system that tracks heart rate, skin conductance, and respiratory rate. The participant is then placed in front of an eye-tracker capable of capturing pupil dilation. Prior to beginning the task, each participant is given a series of instructions by a moderator informing them about the nature of the task and what they are about to see. Once the task begins, the participant is first exposed to a series of standardized images. In an embodiment of the invention, the participant is exposed to at least four standardized images before being exposed to one or more target stimuli. In another embodiment of the invention, the participant is exposed to at least four standardized images after being exposed to one or more target stimuli.

Standardized images for use with the present invention may consist of the same media as the target stimuli. For example, if the target stimuli consist of still images, the standardized images of may be simple still images depicting basic imagery (e.g. animals, furniture, or landscapes). The standardized images may be placed on the screen for a pre-selected amount of time. For instance, the standardized images may be placed on the screen for approximately 5 seconds. In another embodiment, the standardized images are placed on the screen for more than 5 seconds. Following exposure to a standardized image, the participant then sees a blank screen or null exposure. The participant may be exposed to a blank screen for between about 5 seconds and about 15 seconds. Preferably, the participant views a blank screen for about 10 seconds. After temporarily viewing the blank screen, the next standardized image will appear. This process may repeat for multiple standardized images. In one aspect of the invention, the process may repeat for between 4 and 20 standardized images. Preferably, the process will repeat for between 4 and 8 standardized images. In another embodiment of the present invention, the process repeats for more than 8 standardized images. In certain aspects of the invention, more than 8 standardized images may be employed in order to include product-related and/or brand related images.

Following exposure to a series of standardized images, the participant is exposed to at least one target stimulus. The terms "target stimulus" and "target stimuli" refer to whatever media are being evaluated for participant reaction. In an embodiment of the present invention, participants are exposed to target stimuli for at least 5 seconds. In a preferred embodiment of the present invention, participants are exposed to target stimuli for up to 15 seconds. In a most preferred embodiment of the present invention, participants are exposed to target stimuli for more than 5 seconds, but less than 12 seconds. After exposure to each of the at least one target stimulus, the participant then sees a blank screen or null exposure, so that there is a period of no exposure in between the target stimuli and after the final target stimulus. The blank screen is preferably displayed to the participant for at least 10 seconds prior to the next target stimulus or standardized image.

It will be understood that the target stimuli of the present invention may represent any sort of media, and the null exposure will be specific to the media being tested. For instance, the participants may be exposed to noises or music, in which case the participants would experience a period of silence between exposure periods. Other sorts of media for use with the present invention include images, commercials, sounds, music, phrases, print ads, and the like.

Throughout the task, the biometric monitoring system and eye tracker, in addition to other optional measuring devices, are connected (by a wire or wirelessly) to a computerized data processor that can receive the data and apply the described methodologies. As the data is collected, the physiological responses are integrated across channels into a single physiological score.

Using the raw data collected during the task, the Emotional Impact Score is calculated according to the following procedures:
1. The average z-intensity response over the time duration the stimulus was presented is calculated for each participant.
2. After an average z-intensity is calculated for each participant, those values are averaged across all participants to produce a composite average z-intensity.
3. The composite average z-intensity is then compared to a database of scores and given a z-score value based on its relationship to the database mean and distribution.
4. The z-score is the Emotional Impact Score that is plotted on the biphasic graph.
5. The z-score may also be converted to a t-score for additional analyses.

Intensity Score

Each measure of intensity can be associated with point in time or a window or bin of time or event marker within the exposure period. This association can be accomplished using many methods. Preferably, the methodology for associating a measure of intensity with a point in time or a window of time within the exposure period is the same or similar for each measure of engagement determined in a population sample. For example, in one method, a given measure of intensity associated with a change in a biologically based response is assigned to the time slot or window that corresponds to where one half the rise time of that response occurs.

For example, the input to the data processor 16 can be an N by M data matrix where N is the number of subjects and M is the number of time points during which the biological response is recorded. The data processor 16 can include one or more software modules which receive the biological response data and generate the N by M matrix that is used in subsequent processing steps. The data processor 16 can include an intensity processing module which receives the N by M matrix of biological response data, calculates one or more standardized scores for each biological response measured and each time slot. The output can be a total integer score of the intensity of response across subjects in time windows of W seconds width (this is a variable parameter that depends on the presentation). The fractional rise time parameter (f-rise) can be used to estimate the related time window or slot in which the response occurs. For example, if a change in a, biologically based response occurs over three time slots or windows, W1, W2, W3, and one half the rise-time of the response occurred during window W2, the measure of intensity for the change in response would be associated with window W2. Alternatively, the measure of intensity could be associated with the window that contained the peak (i.e., window W3) or the window that contained the trough (i.e., window W1). In addition, a fractional standard deviation parameter (f-std) can be used to estimate the degree of the change in response from baseline.

As a result, for each person, a response map can be determined as a set of intensity values associated with each time (or event) window during which each person was exposed to the presentation. The measure of intensity for the sample population can be determined by adding the measure of intensity associated with the same time window for each person exposed to the presentation. The result is a response time line that is the aggregate of the population sample. The response patterns for two or more biologically based responses (e.g., skin conductivity, heart rate, respiration rate, motion, etc.) can be combined (evenly or unevenly weighted) in a time window by time window basis to determine an overall intensity score or intensity time line. The aggregate can be normalized for a population size, for example 10 or 25 people.

In accordance with the invention, the response map or pattern can be used to evaluate radio, print and audio-visual advertisements (for both television and the Internet), television shows and movies. In one embodiment, a population sample can be exposed to one or more known successful advertisements (TV shows, movies, or websites) and then the same or a different population sample can be exposed to a new advertisement (TV show, movie, or website). Where the response pattern is similar to the response pattern to one or more known successful advertisements (TV shows, movies, or websites) it would be expected that the new advertisement (TV show, movie, or website) would also be successful. Further, a database of response patterns for different types of stimuli (advertisements, TV shows, movies, websites, etc.) could be maintained and analyzed to determine the attributes of a successful advertisement, TV show, movie, or website.

In accordance with the invention, the data processor 16 can include a synchrony processing module which receives the N by M matrix of biological response data, calculates the inverse variance of the rate of change of one or more biological measures across at least a portion of the sample population and determines a standardized value representative of the synchrony for a given time slot. The data processor 16 can determine the synchrony of a given biological response by evaluating the slope of the response in a given time window or event window over the period of exposure for each person in the population sample. For each time window, a slope value can be assigned based on the value of the slope, for example, the greater the slope the greater the slope value. The slope value for each corresponding time window or event window of each person of the population sample can be processed to determine a measure of the variance over the population sample for each time window or event window. For example, the mean and standard deviation of the slope value of the population sample for each time window or event window can be determined and used to further determine the residual variance. The residual variance can be further normalized and used to produce a response pattern that indicates the time-locked synchrony of the response of the population sample to the stimulus.

Similarly, the synchrony response map or pattern can be used to evaluate radio, print and audio-visual advertisements (for both television and the Internet), television shows and movies. Further, the stimuli described can be evaluated using both the intensity response pattern and the synchrony response pattern.

The intensity score can be calculated according to the following steps.

Step 1: Following a noise reduction process for each input channel, for each participant, the distribution of amplitudes of responses including the mean ($\mu$) and standard deviation ($\sigma$) of responses is calculated over some baseline period (this is a variable parameter that depends on the stimulus).

Step 2: For each participant, the location and timing of the trough and peak amplitude of each response is estimated and the difference between each peak and trough (the amplitude of response) is calculated.

Step 3: The values so determined are used to establish a score for each individual response thus: score 0 if the amplitude is less than the baseline $\mu$ for that channel, score 1 for a response if the amplitude is between $\mu$ and $\mu+f-(\sigma)$, and score 2 for a response if the amplitude is greater than $\mu+f-(\sigma)$.

Step 4: Each response score for each participant is assigned to a sequential bin of variable length time-locked to the media stimulus by locating the time of the f-rise.

Step 5: The sum of all the binned response scores across all participants is calculated for each biological sensor. The score is normalized depending on the number of sensors collected (being equal for each test) and the number of participants (being unequal for each test). The score thus created is the intensity score per unit time or per time slot.

Depending on the sensors used and the presentation being experienced, not all channels will be added to the intensity score. For example, certain forms of respiration (such as a sigh indicative of boredom) or motion (taking a drink or looking at a watch) may actually be subtracted from the intensity score. In addition, alternative versions of the intensity measure may be used for presentations with differing goals. For example, when testing a horror movie, sensors such as skin conductance may be weighted more heavily in the calculation because the goal of the content is to generate arousal while testing a comedy, which is meant to elicit laughter, might use stronger weighting towards the respiratory response.

Synchrony Score

Synchrony is a measure of the rate of change of a response by the audience (plural members of the sample population) to a portion of the stimulus or presentation. The audience can be exposed to the stimulus or presentation over a period of time or through a sequence of steps or events. The period of exposure can be divided into windows or portions or events that correspond to elements or events that make up the stimulus or presentation. For example, the synchrony of the response can be determined as a function of the rate of change of a biologically based response to a portion of the stimulus or an event during the presentation by a plurality of audience members or the population sample.

In accordance with the invention, the input to the data processor 16 can be an N by M data matrix where N is the number of subjects and M is the number of time points during which the biological response is recorded. The data processor 16 can include a synchrony processing module which receives the N by M matrix of biological response data, calculates an inverse variance across the matrix values and determines one or more standardized scores for each biological response measured and each time slot. The output will be a total integer score of the synchrony of response across subjects in time windows of W seconds width (this is a variable parameter that depends on the stimulus). In accordance with the invention, the synchrony of a given response is determined by evaluating the rate of change of the response in a given time window or slot over the period of exposure for each participant in the test audience.

The synchrony score can be calculated according to the following steps.

Step 1: Following a noise reduction process for each input channel, create a sliding window of variable width moving forward in time increments that are smaller than the window size.

Step 2: In each window, for each participant, compute the first derivative of one or more of the response endpoints.

Step 3: Across all participants, calculate the mean ($\mu$) and the standard deviation ($\sigma$) of the rate of change in each window.

Step 4: From the above compute a score=$-\ln|\sigma-\mu|$.

Step 5: Scale the resultant score so that all numbers are between 0 and 100.

Step 6: Compute the windowed scores commensurate with the intensity score windows by averaging the sliding scores into sequential windows of variable length time-locked to the media stimulus. The score thus created is the synchrony score per unit time or per time slot.

Engagement Score

The intensity and synchrony scores may be added together to compute the moment-to moment engagement score per unit time or per time slot. Depending on the nature of the test presentation and the test audience, one of the intensity and synchrony scores may be weighted relative to other. For example, for some tests it may be preferred to identify the most extreme responses and thus intensity would be weighted more heavily. Alternatively, different functions can be used to determine different forms of the engagement score. For example, multiplying intensity by synchrony creates exaggerated graphs more readable and usable in some situations such as when evaluating multiple hours of trial testimony, it may be useful to identify the most extreme examples of engagement.

Explicit Emotion Score

To collect information to calculate the Explicit Emotion Score, participants engage in at least a two-part task. The first part of the task involves a Top of the Mind task (TOM), and the second part of the task involves a self-report survey.

The TOM task involves re-exposing the participants to the target stimuli, after which the participants are asked to record the first thing that comes into their mind about each stimulus. The information collected from the TOM task is preferably reserved for qualitative analysis only. Next, the participants are re-exposed to each target stimulus and asked to answer multiple self-report questions about the target stimulus. In one aspect of the invention, participants are provided the target stimulus as a reference while answering the questions about that specific target stimulus. Self-report questions for use with the present invention are designed to probe the level of likeability, the valence of emotional response, and interest for a given stimulus. In one aspect of the invention, responses to questions probing the level of likeability, the valence of emotional response, and the interest for a given stimulus are combined into a single score. In one embodiment, participants are asked to answer three self-report questions. In another embodiment of the invention, participants are asked to answer less than three self-report questions. In yet another embodiment of the present invention, participants are asked to answer more than three self-report questions. In addition to the self-report questions, participants may also be asked to answer additional questions that are not included in the calculation of the explicit emotion score.

Self-report questions may be constructed generally or may be specific to elements of the target stimulus. In the event a participant is asked to respond to multiple target stimuli, the self-report questions are maintained stable across the stimuli.

For example, the participants may be asked to answer the three representative questions below with responses based on a scale of 1 to 9.

1. Please rate how much you disliked vs. liked this [stimulus] using the 9-point scale below.

| very much disliked | | disliked | | neutral | | liked | | Very much liked |
|---|---|---|---|---|---|---|---|---|
| 1 | 2 | 3 | 4 | 5 | 6 | 7 | 8 | 9 |

2. Please rate how bored vs. interested you feel when looking at this [stimulus] using the 9-point scale below.

| very bored | | bored | | neutral | | interested | | very interested |
|---|---|---|---|---|---|---|---|---|
| 1 | 2 | 3 | 4 | 5 | 6 | 7 | 8 | 9 |

3. Please rate how bad vs. good you feel when looking at this [stimulus] using the 9-point scale below.

| very bad | | bad | | neutral | | good | | very good |
|---|---|---|---|---|---|---|---|---|
| 1 | 2 | 3 | 4 | 5 | 6 | 7 | 8 | 9 |

In this aspect of the invention, where the word [stimulus] appears in the questions, a description of the target stimulus is provided. For example, if the target stimulus was a picture, the word picture or image would be used where the word [stimulus] currently appears.

The Explicit Emotion Score can then be calculated using the values provided in each participant's responses to the three questions. First, the values of the self-report questions are averaged across participants for each stimulus. Then the scores are converted to z-scores for the sample. A constant is added to all z-scores. The constant may be between −0.5 and 0.5. In one embodiment of the invention, the constant added to all z-scores is 0.5. The Explicit Emotion z-scores are plotted on the biphasic graph for each stimulus. Additionally, the z-scores are converted to t-score distributions in order to chart the data.

There are many commercially available products and technologies that allow continuous unobtrusive monitoring of biometrically and behaviorally based human responses most often employed for health and fitness purpose. One product, offered under the name LifeShirt System (Vivo-Metrics, Ventura Calif.) is a garment that is worn unobtrusively by a person being evaluated and can simultaneously collect pulmonary, cardiac, skin, posture and vocal information for later analysis. The Equivital system (Hidalgo, Cambridge UK), can collect heart rate, respiration, ECG, 3-axis motion and can integrate sun conductance. Similar features are also offered by the Bioharness system (Zephyr Technologies, Auckland, New Zealand), the Watchdog system (QinetiQ, Waltham, Mass.), BT2 Vital Signs wristwatch (Exmocare, Inc., New York, N.Y.) and Bionode systems (Quasar, San Diego Calif.). Another product, offered under the name Tobii x50 Eye Tracker or Tobii 2150 (Tobii Technology, McLean, Va.) is an eye-tracking device that allows for unobtrusive monitoring of eye-tracking and fixation length to a high degree of certainty. By combining eye-tracking with a biologically based engagement metric, the system can uniquely predict which specific elements within a complex sensory experience (e.g., multimedia presentation or website) are triggering the response. This technology also records additional biometric measures, such as pupillary dilation. Other companies developing this technology include Seeing Machines, Canberra, Australia.

Another technology, developed at the MIT Media Lab, (MIT, Cambridge, Mass.) provides a system for measuring behavioral responses including, but are not limited to, facial micro and macro-expressions, head tilt, head lean, and body position, body posture and body movement. Another technology, developed at the MIT Media Lab, (MIT, Cambridge, Mass.) provides a system for measuring behavioral responses including, but not limited to, the amount of pressure applied to a computer mouse or similar controlling device. In some aspects of the present invention, the eye tracking device may be in the form of goggles or headgear that can be worn while a participant physically holds or manipulates a target stimulus.

While many systems have been put forward for identifying individual emotions, no system has been proposed that can reliably and objectively quantify specific and overall responses to passive and interactive audio, video, and audio-video content. One likely reason for this failure is the complexity and subjectivity of human emotional experience. Rather than use individual biological responses to identify individual emotions in individual participants, the present invention is designed to aggregate biologically based responses of a population to create a moment-to-moment or event based impact of the stimulus or presentation. This can be accomplished according to one embodiment of the invention by determining measures of intensity of responses across the sample population.

As set forth briefly above, the present invention is directed to a method and system for collecting data representative of various biometrically based responses of a person (or animal) to a passive or interactive presentation. The presentation can include an audio, visual or audio-visual stimulus, such as a sound or sequence of sounds, a picture or a sequence of pictures including video, or a combination of one or more sounds and one or more pictures, including video. The stimulus can be pre-recorded and played back on a presentation device or system (e.g., on a television, video display, projected on a screen, such as a movie) or experienced as a live performance. The stimulus can be passive, where the audience experiences the stimulus from a stationary location (e.g., seated in a theater or in front of a television or video screen) or the stimulus can be interactive where the audience is participating in some form with stimulus (e.g., live roller coaster ride, simulated roller coaster ride, shopping experience, computer game, virtual reality experience or an interactive session via the internet). The data collected can be processed in accordance with the invention in order to determine a measure of Emotional impact and the Explicit Emotion of the sample population (or animal).

The measure of Emotional Impact and the Explicit Emotion for a sample population can further be used to predict the level of engagement and impact of a larger population. In the context of this disclosure, the sample population audience can include as many participants as the investigator requires. Furthermore, the period of exposure can be divided into time slots or windows, or event based units and a response value determined for and associated with each time slot or event window.

The system can include three time-locked or synchronized sources of data: 1) a media device for presenting a sensory stimulus or series of stimuli, 2) a monitoring device for the collection of a plurality of biological responses to the sensory stimulus, and 3) an eye-tracking system and/or video camera to determine the location and duration of pupil fixation, dilation and facial responses. Additional video cameras can be used to determine the proximity of the individual and/or audience to the media device and the specific elements of the sensory stimulus being experienced. The biometric response monitoring device and the eye-tracking system and/or video camera can be synchronized with the media device presenting the sensory stimulus so that the monitoring device and the eye-tracking system and/or video camera can consistently record the biometric responses and gaze location, duration and movement, that correspond to same portions of the presentation for repeated exposures to the presentation. The system sensor package can include, but is not limited to, a measure of skin conductivity, heart rate, respirations, body movement, pupillary response, mouse pressure, eye-tracking and/or other biologically based signals such as body temperature, near body temperature, facial and body thermography imaging, facial EMG, EEG, FMRI and the like.

The test media content can include, but is not limited to, passive and interactive television, radio, movies, internet, gaming, and print entertainment and educational materials as well as live theatrical, experiential, and amusement presentations. The three time-locked data sources can be connected (by wire or wireless) to a computerized data processor so the response data can be transferred to the computerized data processor. The computerized data processor can automatically apply the described methodologies of scoring, resulting in a map of engagement per unit time, per event, or aggregated across the entire test sample population or stimuli.

The system is further able to use eye-tracking, directional audio and/or video, or other technology to isolate specific elements or moments of interest for further in-depth processing. In accordance with the invention, the system can track what content is being viewed, who is viewing the content and which physical, behavioral, and biological responses of the audience members correspond to the viewed content on a moment-to-moment basis or on a per event basis.

The system can provide an objective view of how an audience will respond to a passive or interactive presentation. The system can further include a database of biometrically based audience responses, response patterns and audience intensity, synchrony and engagement patterns and levels, and performance metrics (as may be derived therefrom) to a variety of historic media stimuli that, when combined with demographic and other data relevant to the test media content, allows for a prediction of the relative success of that content, presentation or interactive experience.

For the purposes of this invention, the sample audience is preferably at least 20 participants who are monitored viewing the same content one or more times. Monitoring of audiences can be done individually, in small groups, or in large groups, simultaneously or as different times. The audience can be of a tightly defined demographic/psychographic profile or from a broadly defined demographic/psychographic profile or a combination of the two. The system records the time-locked or event locked data streams, calculates the level of moment-to-moment or event based Emotional Impact, and compares the values to a database of similar media content.

The system can use eye-tracking or other technology to isolate specific elements, areas or moments of interest for further analysis or processing. In accordance with the invention, the system can track what content is being viewed, who is viewing the content (including by gender and demographic/psychographic profile), which areas or sub-areas of the content are being focused on by each individual and which measured responses of the audience correspond to the viewed content. Thus, for a given piece of stimulus content in a passive or interactive presentation, the measured responses can be connected with the portion of the content that elicited the response and the data from more than one sample audience or a subset of sample audiences gathered at different times and places can be aggregated.

In accordance with another embodiment, participating members of a household can control their media choice and usage throughout the course of their day while they wear a sensor device (for example, a special article of clothing, a bracelet or other device) that measures some combination of responses as they watch television, listen to music, or use the internet. In this embodiment, the in-home sensing device communicates with an in-home computer or set top box (STB) that determines the nature and timing of the media content the participant has chosen as well as identifying information about the participant. The system would include a technology that could determine the distance from the media stimulus such as distance measurement via technologies like infrared, global positioning satellite, radar or through the acquisition of a signal between two objects, such as the television or computer and participant using technologies with a known range of operation (e.g., WiFi, Zigbee, RFID, or Bluetooth) and/or the direction of the participant eye-gaze (e.g., using eye-tracking technology).

In a variant of this embodiment, the STB or computer can prevent activation of home media devices unless the sensor device was activated to ensure compliance. In another variant of this embodiment, test presentation content and/or broadcast/cable presentation content can be "pushed" to the participant that "matches" a desired demographic/psychographic profile or predetermined level or pattern of engagement. As in prior embodiments, the system can record the lime-locked or event based data streams, calculate the moment-to-moment or event based level of engagement relative to that person, and compare the pattern of engagement to a database of similar individual experiences.

In accordance with another embodiment, the presentation that provides that sensory stimulus can be a live person or persons or activity. This live person or persons may include, but is not limited to, live focus group interactions, live presentations to a jury during a pre-trial or mock-trial, an interview-interviewee interaction, a teacher to a student or group of students, a patient-doctor interaction, a dating interaction or some other social interaction. The live activity can be an activity, for example, riding on a rollercoaster, in a boat or in a car. The live activity can be an everyday activity like shopping in a store, performing yard work or home repair, shopping online or searching the internet. The live activity can also be a simulated or virtual reality based activity that simulates any known or fictional activity.

The present invention relates to a system and method for use in the field of audience measurement. A system is described for recording the biometrically based audience responses to a live or recorded, passive or interactive audio, visual or audio-visual presentation that provides a sensory stimulating experience to members of the audience.

The system can further integrate time-locked or event locked eye-tracking and other video monitoring technology with the measure of engagement to identify specific elements of the sensory stimulus that are triggering the responses. The system can also use the measure of engagement to anticipate the relative success or failure of the test stimulus via predictive models using a database of historic patterns of engagement for similar test stimuli in similar audiences.

Figure 2:
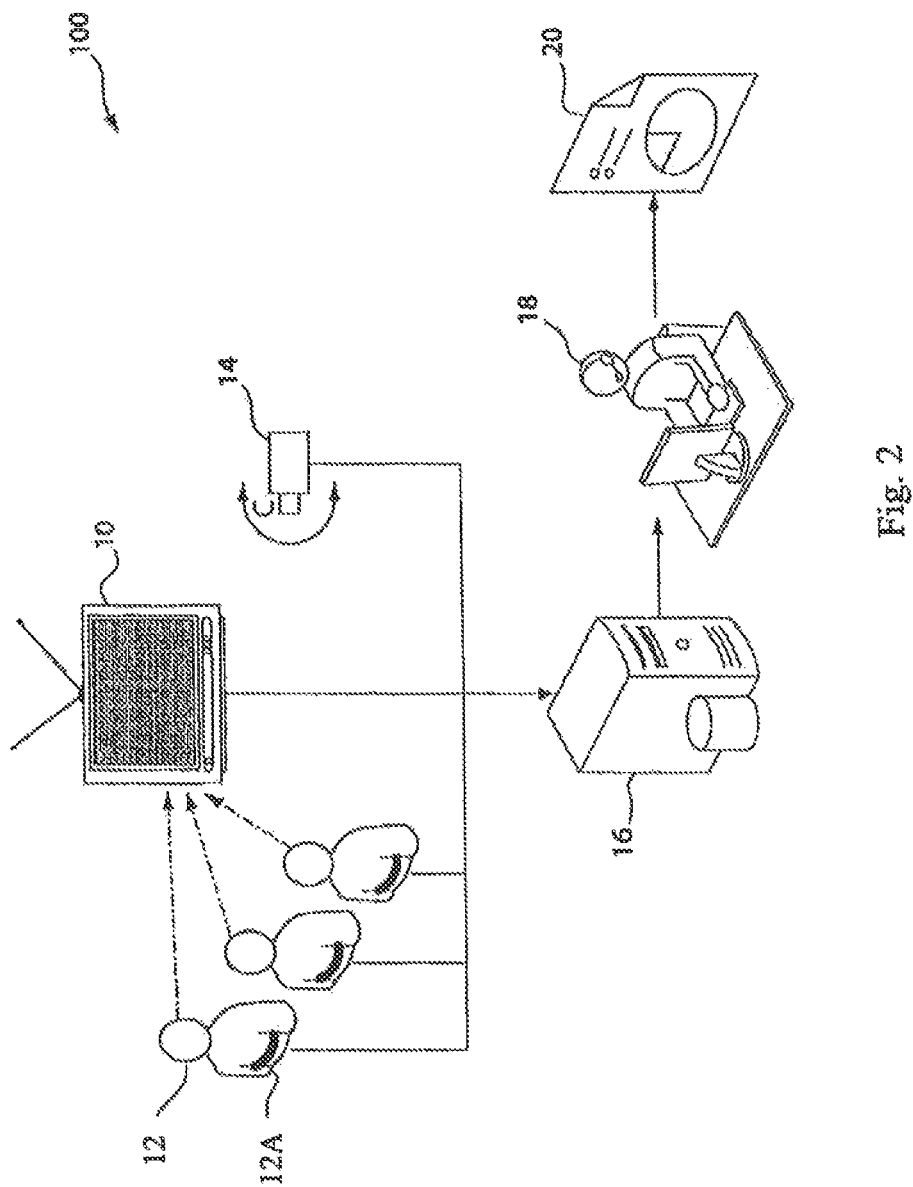
FIG. 2 is a schematic diagram of a system according to an embodiment of the invention for audience measurement in a test theater or facility.

FIG. 2 shows a schematic diagram of an embodiment of the system according to the invention. The presentation is presented to the audience 12 via a display device 10, such as a video display screen or other commercially available technology for presenting the presentation to the test or sample audience 12. The presentation can include, but is not limited to, passive and interactive television, radio, movies, internet, gaming, and print entertainment and educational materials. The display device 10 can include but is not limited to a television, movie screen, a desk-top, hand-held or wearable computer device, gaming console, home or portable music device or any other device for the presentation of passive or interactive audio, visual or audio-visual presentation. For the purposes of this invention, the test audience 12 can be any small or large group defined by any number of parameters (e.g., demographics, level of interest, physiological or psychological profile) who is monitored viewing the content one or more times. The test audience can be monitored using a monitoring system 12A for the collection of a plurality of physical, behavioral, and biological responses and a self-report device 12B for the collection of self-report responses, all time-locked or event locked to each other and the test stimulus or interactive presentation. The system can include a focus and/or facial monitoring system 14 (e.g., eye-tracking system, or one or more digital video cameras C) fir the collection of data on the behavior, facial response and/or precise focus of the individual members of the audience. These data-sources (media stimulus, measured response data, and focus data) can be synchronized or time-locked and/or event-locked to each other whereby the response data collected is associated with a portion of the presentation and sent to a computer data processing device 16. The computer data processing device can be a general purpose computer or personal computer with a processor, memory and software for processing the biological response data and generating the intensity, synchrony and engagement values. The data sources can be time-locked, event-locked or synchronized externally or in the data processor 16 by a variety of means including but not limited to starting them all at the same time, or by providing a common event marker that allows the each system (in data processor 16) collecting the data from the three data sources to synchronize their clocks/event timers or simply synchronizing the clocks in each of the systems or use a common clock. The data processing device 16 can run software that includes the scoring algorithm to calculate the moment-to-moment, event-to-event or total level of Emotional Impact and compares it to a database of other audience responses to the same or similar test presentations, or standardized presentations, and delivers the results to a user-interface 18. The user interface 18 can be provided on a desktop or portable computer or a computer terminal that accesses data processor 16. The user interface 18 can be a web based user interface or provided by a dedicated client miming on the desktop or portable computer or computer terminal. The results can be interpreted and collected into a printed or electronic report 20 for distribution. The response data can be associated with the portion of the presentation that was displayed when the response was measured. Alternatively, the response data can be associated with an earlier portion of the presentation that is presumed to have caused the response based on a determined delay.

The monitoring device 12A for measuring biometric responses can include any of a number of commercially available or other sensors known in the art for measuring such responses. In accordance with the invention, the least invasive and obtrusive sensors with the most comfortable form factor should be chosen to minimize disruption of the experience. Preferably, the sensors should allow participants to experience the presentation or test stimulus "as if" they were not being monitored at all. Form factors include but are not limited to wearable devices such as "smart" garments, watches, and head-gear and remote sensing devices such as microphones, still and video cameras. Many devices are available and known to collect measures of the autonomic nervous system, facial musculature, motion and position, vocal features, eye-movements, respiratory states, and brain waves. Multiple combinations of sensors can be used depending on the sensory stimulus, population, and location of the monitoring.

The self-report device 12B can be any of the well known devices for permitting an audience member to report their response to a presentation or interactive activity. Typically, self-report devices 12B include a knob, a slider or a keypad that is operated by the audience member to indicate their level of interest in the presentation. By turning the knob, moving slider or pressing a specific button on the keypad, the audience member can indicate their level of interest in the presentation or interactive activity. Alternatively, self-report device 12B can be a computer keyboard and/or mouse that an audience member can use to interact with the presentation. Mouse movements in association with icons or elements on the computer screen can be used to indicate levels of interest. In addition, the mouse or other input device can include sensors, such as force and pressure sensors for measuring the forces applied to the mouse by the audience members. Alternatively, keyboard keys (up arrow, down arrow, page up and page down), can used to indicate levels of interest. In addition, the user can type in responses to questions or select answers to multiple choice questions.

Predictive Modeling

The system can further include a database of audience engagement to a variety of historic media or other relevant stimuli or experiences that when combined with demographic/psychographic profiles and other data relevant to the test content that allows for a prediction of the relative success of that content in a similar population. After testing an audience, various forms of the output from the described method can be used to estimate the likelihood of the success of the sensory stimulus in achieving its goal. The statistical analyses for creating predictive models can include, but are not limited to, variables related to the product or the content itself, the price of sale or cost of production of the product or content, the place of purchase or medium of experience, the cost of promotion, and/or the characteristics of the audience. For example, factors included in a model for the television industry may include but are not limited to: a) number of viewers per time slot, b) ratings of the lead-in show, c) ratings of the following show, d) mean ratings for the type of show, e) lead actor/actress popularity rating, f) time of year, g) advertising revenue, h) promotional budget for the show, and/or i) popularity of the network. Other factors may include but are not limited to characteristics of the target audience such as: a) reported liking of the show, b) psychographic characteristics (e.g., introversion vs. extroversion), c) demographic characteristics, and/or d) ability to recall or recognize elements of the show. Indicators of success can include but are not limited to how likely a population with similar characteristics is to watch the television show outside of a testing theater and/or how likely a population with similar characteristics will remember and/or purchase the products being advertised. Preferably, the more people tested (the larger the sample population) and the better characterized the population, the more likely that the model can be an accurate predictor of a larger population response. The preferred predictor model can include, but is not limited to, any of the following statistical methods: a) mixed media models, b) traditional multivariate analyses, e) hierarchical linear modeling, d) machine learning, e) regression analyses, f) Bayesian shrinkage estimators, and/or g) cluster and factor analyses.

Figure 3A:
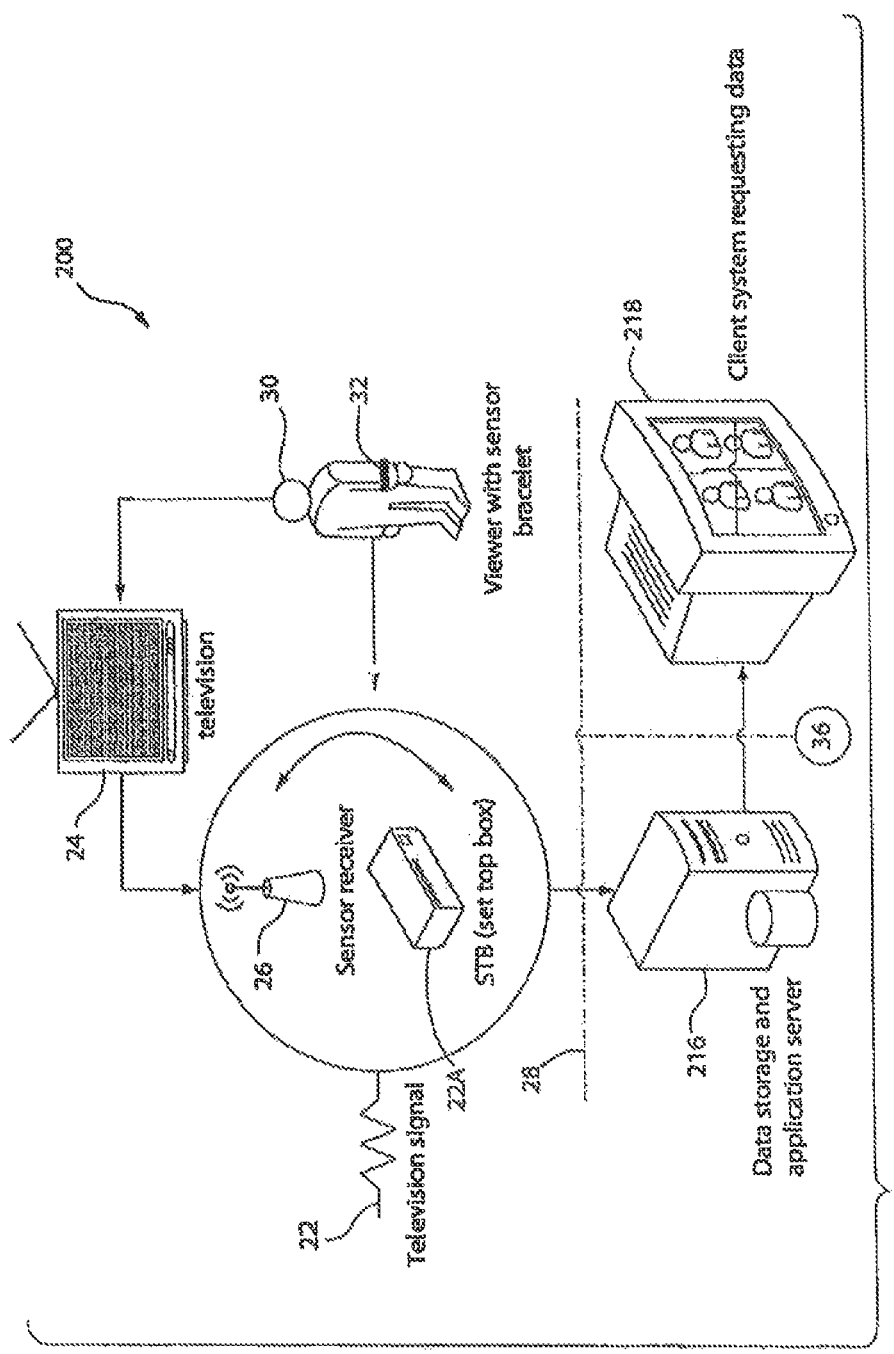
FIG. 3A is a schematic diagram of a second embodiment of the system according to the invention for audience measurement in the home.

FIG. 3A shows a schematic diagram 200 of a second embodiment of the system according to the invention. In this embodiment, the media stimulus is presented via commercially available video signals 22, such as the cable TV signal and plugs into the STB 22A. In turn, the STB 22A enables programs to be displayed on the media device 24 such as a TV monitor, computer, stereo, etc. In this system, a participant 30 in viewing distance wearing a wireless sensor package in an unobtrusive form factor like a bracelet 32 interacts with the media device. In addition, bracelet 32, one or more video cameras (or other known sensing devices, not shown) can be provided to measure, for example, eye tracking and facial expressions and other physical and behavioral responses. As long as that person is in basic viewing distance, the sensor receiver 26, which can be a separate unit or built into the STB 22, will receive information about that participant. The system 200 can time-stamp or event stamp the measured responses along with the unique identifier of that participant. This data can be time-stamped or events stamped with respect to the programming currently being played by the participant. This information can be sent back to a central database 216 via a transmission network 28 such as an internet connection, pager, or cellular network.

Figure 3B:
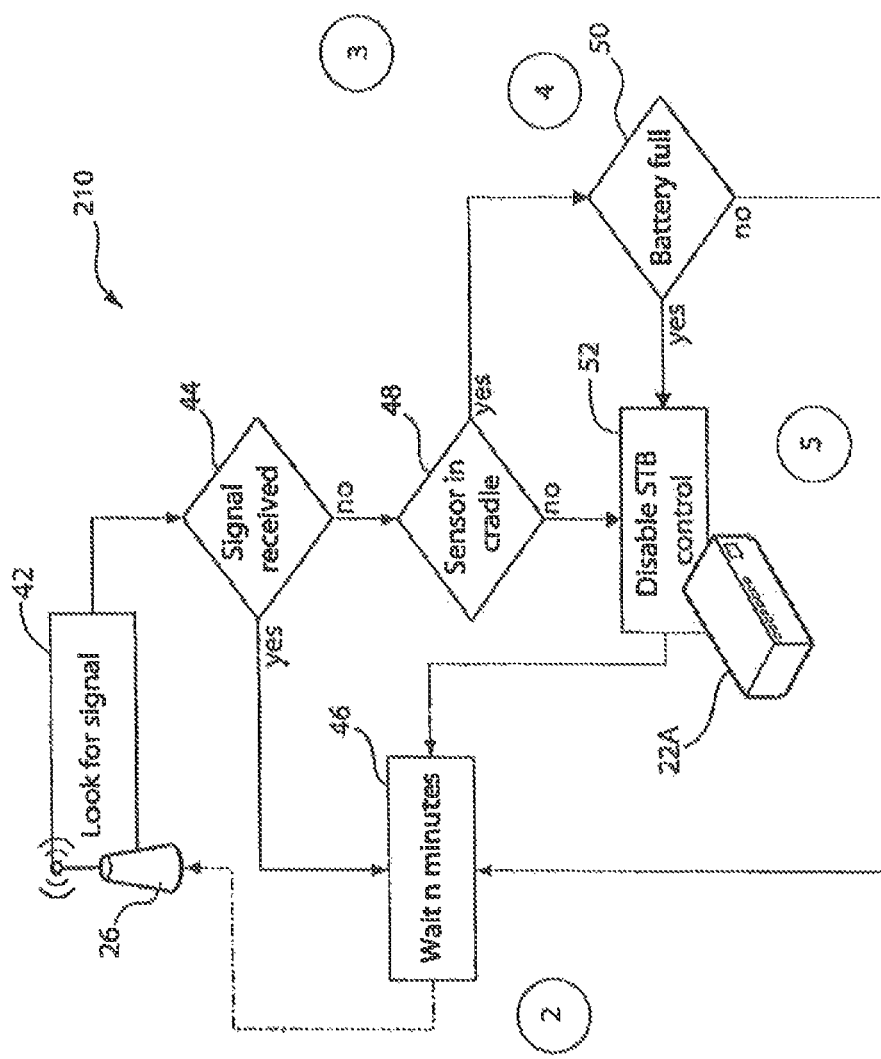
FIG. 3B is a flow diagram of the in-home compliance algorithm for the second embodiment.

FIG. 3B shows a flow diagram 210 of the in-home compliance algorithm to improve usage of the in-home embodiment of this invention. In a household where this system can be set up, compliance can be dealt with by controlling the ability to change programming on the media device being used. The STB 22A can be programmed such that it will not function (partially or completely) if the sensor device is not being worn and is not active. If the sensors are being worn or charging, the STB can be programmed to work. If, however, the sensors are not being worn and are fully charged, the STB can be programmed not to respond fully or partially. In a partial functionality mode, only certain stations may be available, for example, public access and emergency stations. The flow chart 210 of the operation involves a receiver 26 that checks 44 to see if it is getting a signal 42 from the sensor or sensors, which is only possible if the sensor is activated and is being worn. If the receiver is getting a signal, it waits a set amount of time before starting over 46. If it does not receive a signal, the system checks whether a sensor device is being charged in the attached cradle 48, if so and the battery is not full, it also waits a set interval before checking again 50. If, however, the sensor is not active, not charging or fully charged and not being used, the STB can become inactive until the next check shows a change 52.

FIG. 3C shows one aspect of the in-home system, i.e., its ability to identify who in a given household is actually watching. The wireless technology involved in connecting the sensor with the receiver sends out a unique identifier. This identifier will be related to the data sent out in order to identify the source of the biometric data and link it to the current media stimulus. Anyone wearing a sensor but not in the defined wireless range from the receiver will not have their information tracked while outside of that range. The system will wait for a period time 68 if no wireless signal is received. If they are in the range of another receiver 62 (and STB 26) and the signal is received 62, however, their information can be tracked by that system. The flow chart 220 involves a wireless technology 26 (e.g., Bluetooth) that is used to connect the sensor device to the receiver or STB 22A. Wireless communications can be used to establish a connection 66 and transfer data between the receiver (not shown) and the STB 22A as well as to transfer data needed to determine compliance above. Once a participant is identified, information regarding that participant is collected and sent 70 to the database (DB) and processed as above 74 to generate reports for distribution.

Figure 4:
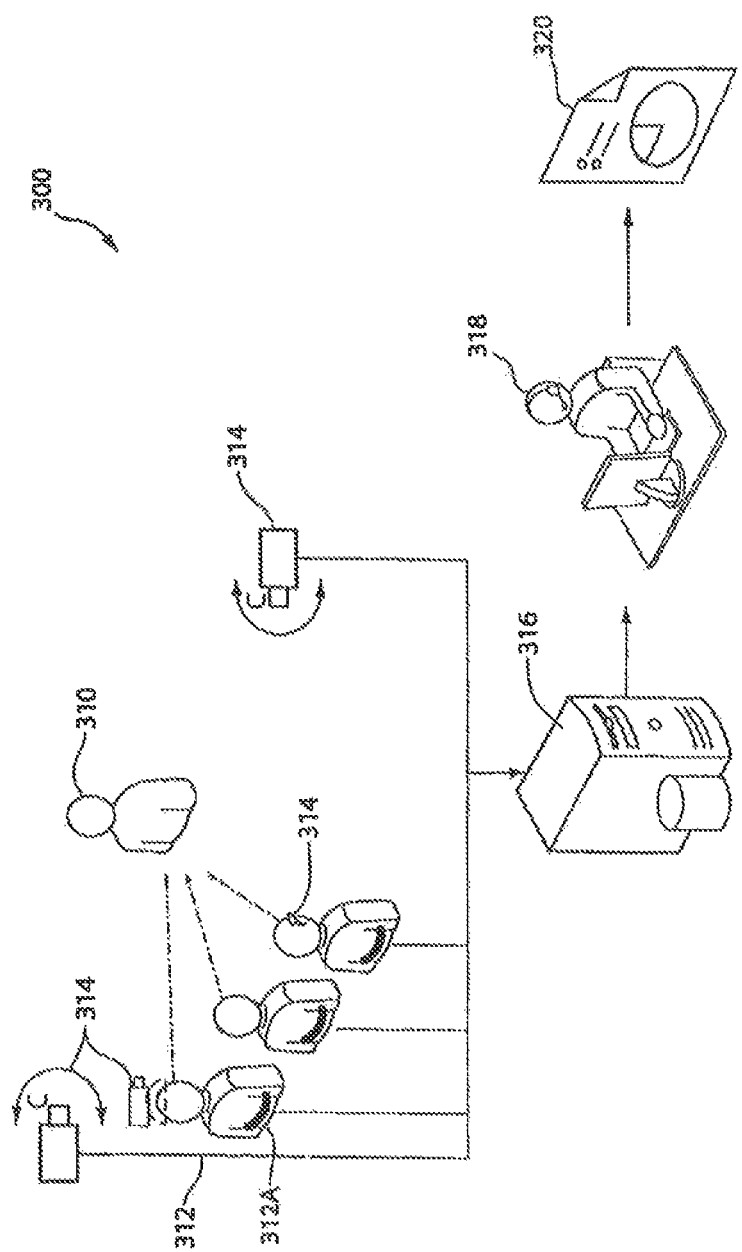
FIG. 4 is a schematic diagram of the third embodiment of the system according to the invention for monitoring levels of engagement during social interaction.

FIG. 4 shows a schematic diagram of the third embodiment of the system 300 according to the invention. In this embodiment, the sensory stimulus can be a live person 310 and the system and method of the invention can be applied to a social interaction that can include, but is not limited to, live focus group interactions, live presentations to a jury during a pre-trial or mock-trial, an interview-interviewee interaction, a teacher to a student or group of students, a patient-doctor interaction, a dating interaction or some other social interaction. The social interaction can be recorded, such as by one or more audio, still picture or video recording devices 314. The social interaction can be monitored for each individual 312 participant's biologically based responses time-looked to each other using a biological monitoring system 312A. In addition, a separate or the same video camera or other monitoring device 314 can be focused on the audience to monitor facial responses and/or eye-tracking, fixation, duration and location. Alternatively, one or more head mounted cameras 314 (for example, helmet mounted or eyeglass mounted) can be used to provide eye tracking data. The data-sources can be time-locked or event locked to each other and sent to a computer data processing device 316. The data processing device 316 can run software that includes the scoring algorithm to calculate the moment-to-moment or event based patterns of engagement and compares it to a database of other audience responses to the same or similar media test stimulus and deliver the results to a user-interface 318. The results can be processed in a predictor model as described above and interpreted and collected into a report 320 for distribution.

In accordance with an alternative embodiment of the invention, an audience (one or more individuals) is exposed to one or more an audio, visual or audio visual stimuli (such as a presentation or items of content) that are interactive and can be separated into events. An event is the exposure or interaction with a stimulus at a specific time and for a specified duration. Typically, the stimuli or presentation can be presented on a computer screen or a large format television screen and can be used in connection with a system that accepts user (audience member) input, using, for example, a mouse, a keyboard or a remote control.

In accordance with an embodiment of the invention, the system can measure one or more responses and event-lock or time-lock the measured response(s) to the portion of the stimuli (for example, the portion of the interactive presentation) being presented to or experienced by the individual audience member at the time of the response. In addition, with respect to eye tracking, the system can record the areas of interest and visual attention of each member of the audience (for which eye tracking is provided and enabled). Areas of Interest can include predetermined target areas, sub-areas, items, creative elements or series of areas or elements within an interactive presentation (or other stimulus) used for individual or aggregated analyses of the interactive activity. Visual Attention can be measured by non-invasive eye-tracking of gaze fixations, locations, and movement for individuals and it can be aggregated for defined user groups and audience population samples.

In accordance with an embodiment of the invention, the system can record biometric measures of each member of the audience for one or more events during the interactive presentation. Biometric measures can include, but are not limited to, pupillary responses, skin conductivity and galvanic skin response, heart rate, heart rate variability, respiratory response, and brain-wave activity. Behavioral type measures can include, but are not limited to, micro and macro facial expressions, head tilt, head lean, body position, body posture, and the amount of pressure applied to a computer mouse or similar input or controlling device. Self-Report type measures can include, but are not limited to, survey responses to items such as perception of the experience, perception of ease-of-use/usability or likeability of experience, level of personal relevance to user, attitude toward content or advertising embedded in the content, intent to purchase product/game or service, and changes in responses from pre-post testing. Self-report measures can also include report of demographic information or the use of psychographic profiling.

Figure 5:
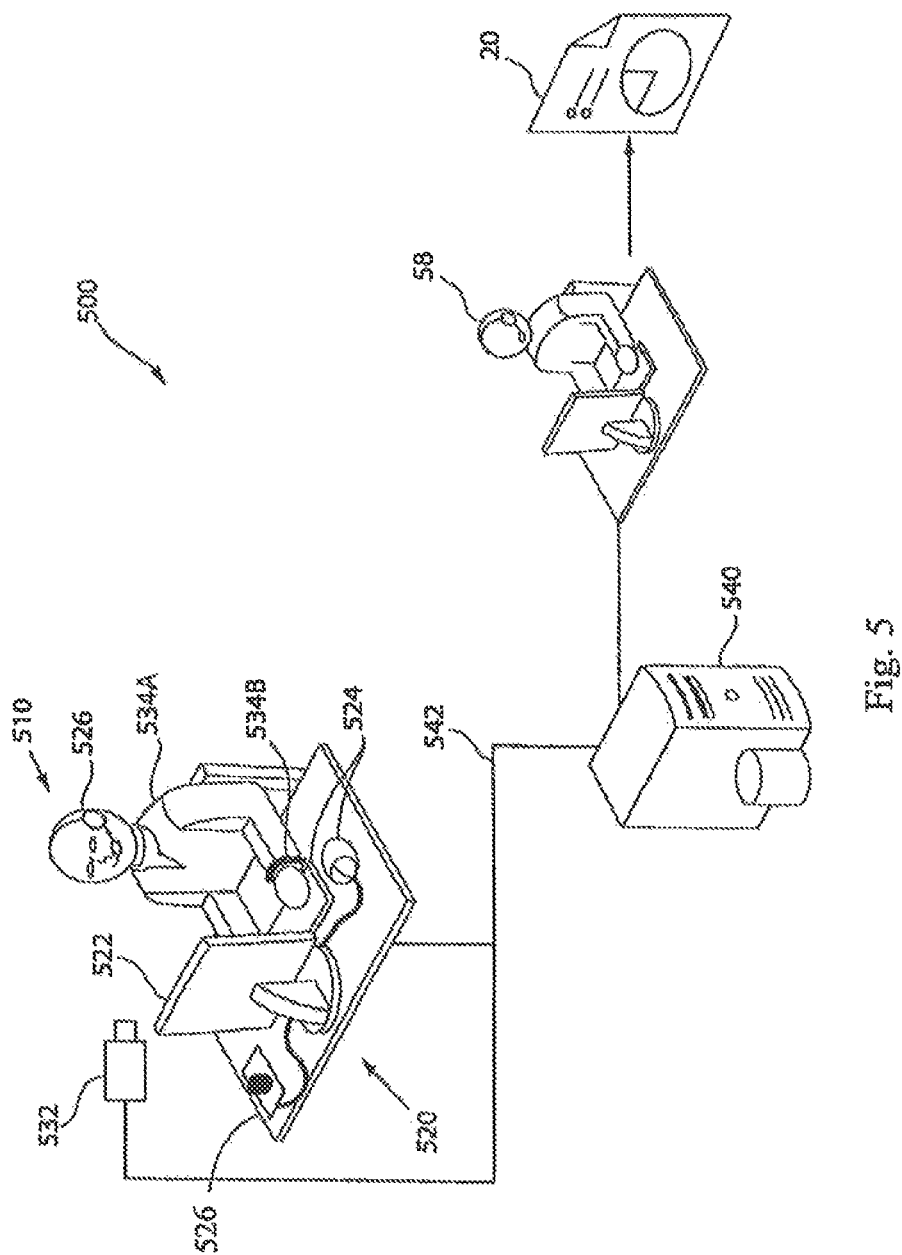
FIG. 5 is a schematic diagram of a system according to an embodiment of the invention for audience measurement of an interactive activity.

FIG. 5 shows a schematic diagram of a system 500 for exposing a member of an audience 510 to an interactive presentation provided on a computer system 520 in accordance with one embodiment of the invention. The user 510 can interact with the presentation provided on the computer screen 522 using a keyboard and/or mouse 524. Sound can be provided by a headset 526 or speakers (not shown). Additional input devices 526 can be used to receive self-report data, such as, like and dislike information in the form of a position of a dial or slider on a hand held device 526 that includes for example a potentiometer.

The user can be monitored using one or more video cameras 532, one or more biometric monitoring devices 534 such as biometric sensing shirt 534A or bracelet 534B. In addition, mouse 522 can include a pressure sensor or other sensor to detect the pressure applied to the mouse buttons. These sensors 532, 534A, 534B can be used for measuring biometric responses such as eye tracking, behavioral and biologic responses. In addition, the computer 520 can be used for measuring and/or recording self-report responses, such as computer generated surveys, free text input via the keyboard 522 or audio responses via headset 526. The data processing system 540 can present the interactive presentation to the user 510 according to a predefined program or sequence and record the eye tracking data as well as other biometric response data in a manner that links the response data to presentation. The data processing system 540 can be connected to the computer system 520 by a wired or wireless network 542 to deliver presentation content to the computer system 520. The wired or wireless network 542 can also be used to deliver sensor response data to data processing system 540 for storage and further processing.

Some or all of the sensor data (such as from sensors 532, 534A and 534B) and input data (such as from input devices 522, 524 and 526) can be transferred either by wire or wirelessly to the computer system 520 and further transferred to data processing system 540. Alternatively, some or all of the sensor and input data can be transferred directly to the data processing system 540 by wired or wireless network 542. Network 542 can utilize most communication technologies, including RS-232, Ethernet, WiFi, Blue Tooth and Zigbee, for example. In addition, more than one communication technology can be used at the same time, for example, network 542 can included wired components (such as, Ethernet and digital cable) and wireless components (such as, WiFi, WiWAX and Blue Tooth) to connect different sensors and computer system components to the data processing system 540.

Furthermore, the data processing system 540 can be one computer system or a cluster or group of computer systems. The response data can be linked or synchronized with the presentation (by aligning using associated timestamps or event windows), whereby the response data is associated with incremental time slots of the presentation. Alternatively, the presentation can be divided into event windows, for example, based on the specific tasks or activities that are included in the interactive presentation and the response data can be associated with event windows associated with specific tasks or portions of a task. Each task or activity can have one or more event windows associated with it and each event window can have the same or a different duration of time.

In accordance with one embodiment of the invention, the eye tracking, behavioral and other biometric measures (either individually or in combination) can be presented to the user to create conscious awareness of these responses and improve the accuracy and utility of the self-report measures. The self report measures can be used in addition to the intensity, synchrony and engagement metrics to evaluate the audience responses to the presentation or activity. The user can be exposed to the interactive presentation and then the user can be exposed to the interactive presentation (or specific portions of the presentation) a second time and provided with information or representative information of their eye tracking, behavioral and other biometric responses and then the user is presented with survey questions (or questionnaires), exposed to one-on-one debriefings or interviews, or involved in qualitative focus groups. Alternatively, inquiries can be made to the user as they view the presentation a second time along with their responses to the presentation.

For each presentation, task, process or experience, one or more Flow, Appeal and Engagement indices can also be determined to aid in the assessment and predictability of the overall audience response. Each of the measures or indices can be determined or computed using a computer system according the invention using one or more methods according to the invention. The preferred embodiment, one or more of the measures or indices can be determined by a computer software module running on a computer system according to the invention. The computer software module can be a stand alone program or component of a larger program and can include the ability to interact with other programs and/or modules or components.

In accordance with one embodiment of the invention, computer system can include a computer software module that records, by storing in memory of the computer system, the biometric and other data produced by the biometric sensors and video cameras. The stored biometric and other data can be associated with a point in time within the time duration of the presentation or an event window of an activity that serves as the stimulus. This can be accomplished by storing one or more data values paired with or linked to a time value or using a database that associates one or more stored data values with one or more points in time. After the presentation has ended or the activity is completed, software running on the computer system can process the stored biometric and other data to determine the various measures and indices. Alternatively, the stored data can be transferred to another computer system for processing to determine the various measures and indices.

The Biometric Cognitive Power index for an event window (or a time slot or time window) can be determined as a function of the portion of the event time (duration or frequency) during an interactive task, process or experience where the cognitive response (value, amplitude or rate of change of value or amplitude) such as, the pupillary response, is above a predefined threshold (for example, above or below the mean or average response by k*standard deviation, where k can be, for example, 0.5, 1.0, 1.5). In other embodiments, other measures of cognitive response can be used as an alternative to or in addition to pupillary response, such as EEG or brain wave activity.

Biometric Cognitive Power index (e) for an event e, can be determined as the sum of the number of time instants ti (or the portion or percentage of time) in the first T seconds of each subject's experience (which is referred to as the subject's analysis-duration T) where the cognitive response measured is above the predefined threshold and averaged across all subjects viewing the same experience/stimulus. In particular, $$\text{Biometric Cognitive Power}(e) = \text{Average}[\text{across all subjects } s](\text{sum of (cognitive\_response } (s,ti)))$$

where ti<T and cognitive response (pupil_response)>specified threshold

In one embodiment of the invention, the analysis-duration T can be set to the first 5 seconds of the subjects' experience of the event. In other embodiments, it can be, for example, set between 5-10 seconds. In other embodiments, it can be set to one-half or one-third of the event duration or time window.

In one embodiment of the invention, a time instant ti can be the sampling rate of the system for the biometric sensor, for example, 20 msec. In other embodiments, other units of time can be used, such as 0.10 sec. and 0.01 sec.

Where, in this example, the cognitive response measured is a pupillary response function. The function, pupil_response (s, ti) can be the response of subject a during event window eat time instant ti, if the response differs from the average response for subject s on event e by more than k*standard deviation, where k can be an analysis-specific threshold or parameter, for example, between 0.5 and 1.5. The length of the analysis-duration can be specific to each stimulus image, event or scene of the presentation.

In accordance with one embodiment of the invention, the analysis-duration T can be determined as one half to one-third the time needed for an average individual to process the information shown in the image, event or scene of the presentation. For instance, if the presentation consists primarily of a textual document or print material then analysis-duration T can be, for example, set in the range of 15-45 seconds and begin at the start of the time window or event window or within, for example, the first 15 seconds of the time or event window. If the image, event or scene consists primarily of visual objects/drawings as in a print ad (with very little text information), then the analysis-duration T can be set in the range of 5 to 10 seconds. In an alternative embodiment of the invention, the analysis-duration can be set to the first 5 seconds of an event window or time window. In other embodiments, the analysis-duration T, can be any unit of time less than or equal to the event window or time window and can begin at any point during the event window or the time window. For interactive activities, for example shopping, the event window can be a unit of time during which the audience member selects an item for purchase, makes a purchase or returns an item and the analysis duration T can begin approximately at the point in time when the audience member selects an item for purchase, make a purchase or returns an item.

In accordance with one embodiment of the invention, the Biometric Cognitive Power index determination can be implemented in a computer program or computer program module that accesses biometric data stored in memory of a computer system, receives the data from another program module or receives it directly from biometric sensors. The data can be real time data or data that was previously captured from one or more audience members and stored for later processing.

In accordance with one embodiment of the invention, the parameters, including k and the analysis-duration T can be computed using predictive models described in any of the data mining books described herein, by utilizing outcome variables such as a subjects' (or audience member's) behavior (e.g., purchase/return of a product described in the stimulus or event). The data mining books include: Larose, Daniel T., Data Mining Methods and Models, John Wiley & Sons, Inc., 2006; Han, Micheline Kamber Jiawei, Data Mining: Concepts and Techniques, Second Edition (The Morgan Kaufmann Series in Data Management Systems), Elsevier, Inc., 2006; Liu, Bing, Web Data Mining: Exploring Hyperlinks, Contents, and Usage Data (Data-Centric Systems and Applications), Springer-Verlag, 2007; and Berry, Michael J. A. and Linoff, Gordon S., Data Mining Techniques: For Marketing, Sales, and Customer Relationship Management, John Wiley & Sons, Inc., 1997; all of which are herein incorporated by reference in their entirety.

For visual stimuli, such as images, we can, for example, represent the 2-dimensional screen area as composed of a grid of size m-by-n cells or pixels. The m and n values will depend on the parameters of the visual stimulus and the computer or TV screen on which the visual stimulus is presented and can be the pixel resolution of the presentation screen or determined as a function of the pixel resolution of the presentation screen. Typically, m-by-n will be 1280-by-1024 or 640-by-480. In on embodiment of the invention, the visual screen can be a 1280-by-1024 grid of pixels and the stimulus grid can be represented by a matrix of grid cells, for example as 640-by-512 (by defining a grid cell as a 2×2 matrix of pixels).

Gaze location can be defined as a set of grid-cells that are determined to be the focus of an audience member's gaze and represent the set of grid cells (0–(m*n)) that an audience member looked at during a time or event window. If the audience member focused on one grid cell, the gaze location would be one the grid cell, whereas, if the audience member focused on more than one grid cell, the gaze location would be a set of grid cells or a function of the set of grid cells (such as the grid cell or set of contiguous grid cells that were the focus for the longest time). Where a grid cell is defined as more than one pixel, audience member focus on any of the pixels in the grid cell is considered gaze on the location of the grid cell. A gaze location can be used to identify a contiguous area using a set of grid cells on the screen. Alternatively, a gaze location can also represent a group of such contiguous areas, each area being disjoint from one another.

A Biometric Cognitive Map can be produced by plotting the areas of individual or aggregated group gaze fixation as a function of a biometric cognitive power index (where the duration or frequency of cognitive response are above a threshold level) and the gaze locations on the presentation (or image, event or scene therein) corresponding to the cognitive power index when the stimulus has a visual component, such as an image or a video. A biometric cognitive map can be used to identify the areas of a presentation that are associated with higher levels of responses indicative of high levels of cognitive activity. Specifically, a biometric cognitive map represents the gaze locations or aggregated regions of the locations on the visual portion of the stimulus when the cognitive response for a subject differs from its mean by k*standard deviation, for example, where k can be between 0.5 and 1.5 during the analysis-duration for the subject's experience. The gaze locations can be aggregated either across temporal instants for each subject (e.g., a subject 's' looking at a location at instants "h" and "h+5") within the analysis-duration, or across different subjects looking at the locations within the analysis-duration of their experience. A variety of clustering algorithms, such as those described in data mining hooks disclosed herein, can be employed to create aggregated regions or clusters from a set of specific gaze locations.

In accordance with one embodiment of the invention, the Biometric Cognitive map can be generated by a computer program, computer program module or a set of computer program modules that access biometric cognitive power index data and gaze fixation data that was stored in memory of a computer system, received from another program module or received directly from biometric sensors and the eye tracking system. The data can be real time data or data that was previously captured and stored from one or more audience members.

In accordance with one embodiment of the invention, a biometric cognitive plot area can be determined by first plotting gaze locations in a cognitive map, such as for a specific time or event window, then creating clusters or aggregated regions and determining the area or relative area of dusters.

In accordance with one embodiment of the invention, the system, in accordance with the method of the invention, can plot the gaze locations that correspond to significant cognitive responses (responses that meet or exceed a threshold) in a biometric cognitive map for a stimulus (or an event) for all subjects exposed to the stimulus for a period more than the analysis-duration. This can, for example, be implemented in a computer program, a computer program module or set of computer program modules. The gaze locations can be plotted only when the cognitive response for a subject is, for example, above or below differs from) the subject's mean response by k*std_deviation, where, for example, k can be between 0.5 and 1.5. If the response is above the mean, the location can be termed a location of high cognitive response and the locations can be considered high cognitive locations. If the response is below the mean response, the location can be termed a location of low cognitive response and the locations can be considered low cognitive locations.

In addition, adjacent high locations and/or adjacent low locations can be combined based on their proximity (distance to each other) using well known clustering algorithms. Examples of clustering algorithms are disclosed in the data mining books disclosed herein.

In accordance with one embodiment of the invention, the clustering can be accomplished as follows:
1) For each grid cell identifying a high or low location, expand the set of grid cells to include all its neighboring grid cells, 5 grid cells in all directions (i.e., expanding by a circle of radius of 5 centered at the grid cell) in the cluster. Alternate radii of 10-15 grid cells may also be employed.
2) The cluster for a set of grid cells of a kind (high or low) can thus include any 'unfilled gaps' (unselected grid cells in the area) and identify one or more contiguous 'geometric regions' in the cognitive map.
3) The low cognitive clusters in a cognitive map will cluster the low cognitive locations and the high cognitive clusters in a cognitive map will cluster the high cognitive locations.
4) The clustering algorithm can be applied iteratively starting with a single grid cell (or pixel) or set of contiguous grid cells (or pixels) and repeated until a predetermined number of clusters are defined.

The biometric cognitive plot area can have low and high cognitive clusters identified on or defined for a cognitive map. The system, according to the method of the invention, can determine the biometric cognitive plot area by determining the total area of the high and/or the low cognitive clusters. The biometric cognitive plot area can be measured in terms of the number of pixels or grid cells in a cluster or group of clusters, or as a proportion (or percentage) of the total area of the presentation screen or a portion of the presentation screen (such as, a quadrant or a region).

In accordance with one embodiment of the invention, the Biometric Cognitive plot area can be determined using a computer program, computer program module or a set of computer program modules that access biometric data and gaze fixation data, and/or intermediate data constructs (such as, the Biometric Cognitive Power index), that were stored in memory of a computer system, received from another program module or received directly from biometric sensors and the eye tracking system. The data can be real time data or data that was previously captured and stored from one or more audience members.

The Biometric Emotive Power index for an event window (or a time slot or time window) can be determined as a function of the portion of the event time (duration or frequency) during an interactive task, process or experience where the emotive response (value, amplitude or rate of change of value or amplitude) such as one or more of skin conductance, heart rate, and respiratory responses, is above a predefined threshold (e.g., above or below the mean or average response by k*standard deviation, where k can be, e.g., 0.5, 1.0, 1.5). In other embodiments, other measures of emotive response can be used as an alternative to or in addition to skin conductance, heart rate and respiratory responses, such as brain wave activity.

Biometric Emotive Power index (e) for an event e, can be determined as the sum of the number of time instants ti (or the portion or percentage of time in the first T seconds of each subject's experience (which is referred to as the subject's analysis-duration T) where the emotive response measured is above the predefined threshold and averaged across all subjects viewing the same experience/stimulus. For example, Biometric Emotive Power(e)=Average[across all subjects s](sum of (emotive_response(s,ti))

where ti<T and emotive response (skin_conductance_response)>specified threshold.

In one embodiment of the invention, the analysis-duration T can be set to the first 5 seconds of the subjects' experience of the event. In other embodiments, it can be, for example, set between 5-10 seconds. In other embodiments, it can be set to one-half or one-third of the event duration or time window.

In one embodiment of the invention, a time instant ti can be the sampling rate of the system for the biometric sensor, for example, 20 msec. In other embodiments, other units of time can be used, such as 0.10 sec. and 0.01 sec.

Where, in this example, the emotive response measured is a skin conductance response function. The function, skin_conductance_response (s, ti) can be the response of subject s during event window e at time instant ti, if the response differs from the average response for subject a on event e by more than k*standard deviation, where k can be an analysis-specific threshold or parameter, for example, between 0.5 and 1.5. The length of the analysis-duration can be specific to each stimulus image, event or scene of the presentation.

In accordance with one embodiment of the invention, the analysis-duration T can be determined as one half to one-third the time needed for an average individual to process the information shown in the image, event or scene of the presentation. For instance, if the presentation consists primarily of a textual document or print material then analysis-duration T can be, for example, set in the range of 15-45 seconds and begin at the start of the time window or event window or within, for example, the first 15 seconds of the time or event window. If the image, event or scene consists primarily of visual objects/drawings as in a print ad (with very little text information), then the analysis-duration T can be set in the range of 5 to 10 seconds.

In an alternative embodiment of the invention, the analysis-duration can be set to the first 5 seconds of an event window or time window. In other embodiments, the analysis-duration T, can be any unit of time less than or equal to the event window or time window and can begin at any point during the event window or the time window. For interactive activities, for example shopping, the event window can be a unit of time during which the audience member selects an item for purchase, makes a purchase or returns an item and the analysis duration T can begin approximately at the point in time when the audience member selects an item for purchase, make a purchase or returns an item.

In accordance with one embodiment of the invention, the Biometric Emotive Power index determination can be implemented in a computer program or computer program module that accesses biometric data stored in memory of a computer system, receives the data from another program module or receives it directly from biometric sensors. The data can be real time data or data that was previously captured from one or more audience members and stored for later processing.

In accordance with one embodiment of the invent ion, the parameters, including k and the analysis-duration T can be computed using predictive models described in any of the data mining books described herein, by utilizing outcome variables such as a subjects' (or audience member's) behavior (e.g., purchase ret of a product described in the stimulus or event).

For visual stimuli, such as images, we can, for example, represent the 2-dimensional screen area as composed of a grid of size m-by-n cells or pixels. The m and n values will depend on the parameters of the visual stimulus and the computer or TV screen on which the visual stimulus is presented and can be the pixel resolution of the presentation screen or determined as a function of the pixel resolution of the presentation screen. Typically, m-by-n will be 1280-by-1024 or 640-by-480. In on embodiment of the invention, the visual screen can be a 1280-by-1024 grid of pixels and the stimulus grid can be represented by a matrix of grid cells, for example as 640-by-512 (by defining a grid cell as a 2×2 matrix of pixels).

Gaze location can be defined as a set of grid-cells that are determined to be the focus of an audience member's gaze and represent the set of grid cells (0–(m*n)) that an audience member looked at during a time or event window. If the audience member focused on one grid cell, the gaze location would be one the grid cell, whereas, if the audience member focused on more than one grid cell, the gaze location would be a set of grid cells or a function of the set of grid cells (such as the grid cell or set of contiguous grid cells that were the focus for the longest time). Where a grid cell is defined as more than one pixel, audience member focus on any of the pixels in the grid cell is considered gaze on the location of the grid cell. A gaze location can be used to identify a contiguous area using a set of grid cells on the screen. Alternatively, a gaze location can also represent a group of such contiguous areas, each area being disjoint from one another.

A Biometric Emotive Map can be produced by plotting the areas of individual or aggregated group gaze fixation as a function of a biometric emotive power index (where the duration or frequency of emotive response are above a threshold level) and the gaze locations on the presentation (or image, event or scene therein) corresponding to the emotive power index when the stimulus has a visual component, such as an image or a video. A biometric emotive map can be used to identify the areas of a presentation that are associated with higher levels of responses indicative of high levels of emotive activity. Specifically, a biometric emotive map represents the gaze locations or aggregated regions of the locations on the visual portion of the stimulus when the emotive response for a subject differs from its mean by k*standard deviation, for example, where k can be between 0.5 and 1.5 during the analysis-duration for the subject's experience. The gaze locations can be aggregated either across temporal instants for each subject (e.g., a subject 's' looking at a location at instants "h" and "h+5") within the analysis-duration, or across different subjects looking at the locations within the analysis-duration of their experience. A variety of clustering algorithms, such as those described in data mining books disclosed herein, can be employed to create aggregated regions or clusters from a set of specific gaze locations.

In accordance with one embodiment of the invention, the Biometric Emotive map can be generated by a computer program, computer program module or a set of computer program modules that access biometric emotive power index data and gaze fixation data that was stored in memory of a computer system, received from another program module or received directly from biometric sensors and the eye tracking system. The data can be real time data or data that was previously captured and stored from one or more audience members.

In accordance with one embodiment of the invention, a biometric emotive plot area can be determined by first plotting gaze locations in a emotive map, such as for a specific time or event window, then creating clusters or aggregated regions and determining the area or relative area of clusters.

In accordance with one embodiment of the invention, the system, in accordance with the method of the invention, can plot the gaze locations that correspond to significant emotive responses (responses that meet or exceed a threshold) in a biometric emotive map for a stimulus (or an event) for all subjects exposed to the stimulus for a period more than the analysis-duration. This can, for example, be implemented in a computer program, a computer program module or set of computer program modules. The gaze locations can be plotted only when the emotive response for a subject is, for example, above or below (i.e., differs from) the subject's mean response by k*std_deviation, where, for example, k can be between 0.5 and 1.5. If the response is above the mean, the location can be termed a location of high emotive response and the locations can be considered high emotive locations. If the response is below the mean response, the location can be termed a location of low emotive response and the locations can be considered low emotive locations.

In addition, adjacent high locations and/or adjacent low locations can be combined based on their proximity (distance to each other) using well known clustering algorithms. Examples of clustering algorithms are disclosed in the data mining books disclosed herein.

In accordance with one embodiment of the invention, the clustering can be accomplished as follows:

1) For each grid cell identifying a high or low location, expand the set of grid cells to include all its neighboring grid cells, 5 grid cells in all directions (i.e., expanding by a circle of radius of 5 centered at the grid cell) in the cluster. Alternator radii of 10-15 grid cells may also be employed.
2) The cluster for a set of grid cells of a kind (high or low) can thus include any 'unfilled gaps' (unselected grid cells in the area) and identify one or more contiguous 'geometric regions' in the emotive map.
3) The low emotive clusters in an emotive map will cluster the low emotive locations and the high emotive clusters in an emotive map will cluster the high emotive locations.
4) The clustering algorithm can be applied iteratively starting with a single grid cell (or pixel) or set of contiguous grid cells (or pixels) and repeated until a predetermined number of clusters are defined.

The biometric emotive plot area can have low and high emotive clusters identified on or defined for an emotive map. The system, according to the method of the invention, can determine the biometric emotive plot area by determining the total area of the high and/or the low emotive clusters. The biometric emotive plot area can be measured in terms of the number of pixels or grid cells in a cluster or group of clusters, or as a proportion (or percentage) of the total area of the presentation screen or a portion of the presentation screen (such as, a quadrant or a region).

In accordance with one embodiment of the invention, the Biometric Emotive plot area can be determined using a computer program, computer program module or a set of computer program modules that access biometric data and gaze fixation data, and/or intermediate data constructs (such as, the Biometric Emotive Power index), that were stored in memory of a computer system, received from another program module or received directly from biometric sensors and the eye tracking system. The data can be real time data or data that was previously captured and stored from one or more audience members.

The eye tracking system can monitor the gaze fixation of each user, on a moment by moment basis or an event basis. The gaze fixation data can be used to identify elements, areas or regions of interest, including areas that the user or a group of users (that make up the sample audience) spent more time looking at than other areas of a presentation or correspond to or are associated with higher cognitive or emotive responses than other areas. The system can analyze the eye tracking and the response data and determine or calculate the plot area of the region, area or element within the presentation that corresponds to a response or combination of responses. The plot area can define the peripheral boundary of an area or region that is of interest.

Using the eye tracking response data and the biometric response data, one or more biometric cognitive maps and biometric emotive maps can be generated and the biometric cognitive and emotive plot area for each cognitive and emotive map can also be determined. In accordance with one embodiment of the invention, the Cognitive and Emotive Visual Coverage indices for a category of stimuli (for example, products) can be determined as function of the biometric cognitive and emotive plot areas. In one embodiment, the Visual Coverage index can be determined as function of the areas of the presentation that are associated with either high or low (cognitive or emotive) response and the total area of the presentation screen or the presentation on the screen.

High Cognitive Visual Coverage Index=High Cognitive plot area/Total Area

Where the High Cognitive plot area is the sum of the area of all the high cognitive clusters for the stimulus and the Total Area is the total area of the presentation gaze area (where the presentation occupies less than the whole screen) or the screen.

High Emotive Visual Coverage Index=High Emotive plot area/Total Area

Where the High Emotive plot area is the sum of the area of all the high emotive clusters for the stimulus and the Total Area is the total area of the presentation gaze area (where the presentation occupies less than the whole screen) or the screen.

Low Cognitive Visual Coverage Index=Low Cognitive plot area/Total Area

Where the Low Cognitive plot area is the sum of the area of all the low cognitive clusters for the stimulus and the Total Area is the total area of the presentation gaze area (where the presentation occupies less than the whole screen) or the screen.

Low Emotive Visual Coverage Index=Low Emotive plot area/Total Area

Here the Low Emotive plot area is the sum of the area of all the low cognitive clusters for the stimulus and the Total Area is the total area of the presentation gaze area (where the presentation occupies less than the whole screen) or the screen.

Where at least one biometric cognitive map and at least one biometric emotive map are generated, cognitive coverage indices (high and low) and emotive visual coverage indices (high and low) can be determined for each task, process, experience or event.

In accordance with one embodiment of the invention, a Visual impact index (or area) can be determined as function of the cognitive and emotive coverage indices. The High Visual Impact index (or area) for a stimulus or category of stimuli (or products) can be determined as the average or the sum of the emotional and cognitive coverage indices.

For example, in accordance with one embodiment of the invention the High Visual impact index (or area) for a stimulus or category of stimuli (or products) can be, for example, determined as:

(High Emotional Visual Coverage Index+High Cognitive Visual Coverage Index)

The Low Visual Impact index (or area) for a stimulus or category of stimuli (or products) can be, for example, determined as:

(Low Emotional Visual Coverage Index+Low Cognitive Visual Coverage Index)

In accordance with an embodiment of the invention, each of the computed biometric measures described herein, such as, intensity, synchrony, engagement, emotional power index, cognitive power index, emotional coverage index, biometric coverage index and visual impact for a stimulus can be used to predict or estimate the success rate of the stimulus on a stand-alone or on a comparative basis to other stimuli. The success can be measured by the external response measures of the general or target audience outside the test facility to the content, product or brand represented in the stimuli. The external response measures can include but is not limited to the number of viewers watching, downloading and/or storing, or skipping/forwarding the stimulus (overall viewing characteristics), the number of comments or amount of buzz that the stimulus or the content referred to in the stimulus generates in offline or online (internet) forums, social networks, communities and/or markets, the number of views of the stimulus (by audience members) in offline or online (internet) forums, social networks, communities and markets, the average rating for the stimulus by the audience, the overall adoption rate (the volume of product sales) by target audience etc.

Figure 6:
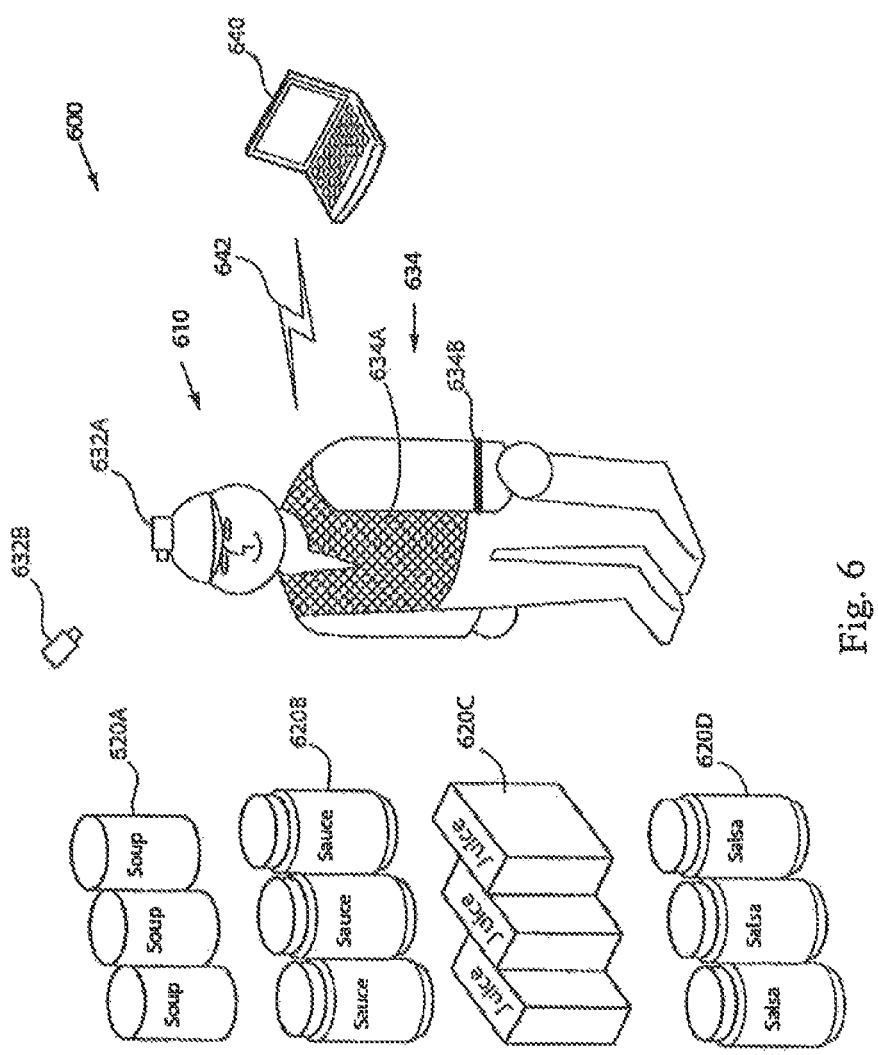
FIG. 6 is a schematic diagram of a system according to an embodiment of the invention for audience measurement of an alternate interactive activity.

In accordance with one embodiment of the invention 600, as shown in FIG. 6, a sample population of shoppers 610 (individuals seeking to purchase a specific product or product type) can be studied by exposing them to an active or passive presentation which includes a set of products 620 or products of a specific type. For example, different types and/or brands of Soups 620A, Sauces 620B, Juices 620C, and Salsas 620D can be presented, such as on a store shelf. Each shopper 610 can be monitored while actually shopping in a store for (or being presented with a simulated environment or diagram of a store or supermarket shelf showing) different products, for example, juices, salsas, sauces or soups), all by the same or a different company (same brand or different companies and brands) and asked to select one or more for purchase, for example, by taking the product off the shelf or selecting with a mouse or dragging an icon to a shopping cart.

Where the shopper is actually shopping in a store, the shopper can be fitted with a camera that is directed to show what the shopper is looking at, for example a helmet mounted camera 632A, or a camera mounted on eye glasses worn by the shopper (not shown). Thus, the camera 632A can show what the shopper 610 is looking at during any given time slot or event window. In addition, the shopper can be monitored using one or more biometric monitoring devices 634 worn by the shopper during the experience, such as biometric sensing shirt 634A or bracelet 634B. Additional cameras 632B can be provided (either mounted or hand held) in the area of the store that the shopper is viewing to provide pupillary response data.

The response data can be stored in the monitoring devices 634 (or one or more memory devices associated with one or more of the monitoring devices) worn by the user, or transferred by wire (not shown) or wirelessly over network 642 to data processing system 640, shown as a portable computer, although a desktop computer or group of computers, can be used as well. Depending on the type of network used, the data processing system can located in any location that can be connected to the network 642, such as within the store, across the city or across the country. The network 642 can be made up of several communication channels using one technology or a combination of technologies (Ethernet, WiFi, WiMAX, Blue Tooth, ZigBee, etc.).

Where the data is stored in the monitoring devices (or one or more memory devices associated with one or more of the monitoring devices) a network 642 can be used to transfer the data to the data processing system 640 after the task or presentation or a set of tasks or presentation is paused or completed. Alternatively, the stored data can be transferred to the data processing system 640 by direct wire connection (not shown) as well. As described here, the data processing computer can process the sensor and camera data to generate the various indices described herein.

Alternatively, the shopper can be fitted only with a helmet mounted camera 632A or eye glass mounted camera (not shown) and sent on a shopping spree. The shopper can be presented with a video of the shopping experience on a computer, television or video screen while being monitored using a system according to an embodiment of the invention, such as shown in FIG. 5. Thus, an eye tracking system 532 and a combination of biometric and behavioral sensing devices 534A, 534B and input devices 534, 526, 528 can be used to monitor response data associated with the activity and transfer the response data to the data processing system 540 for further processing. Alternatively, the shopper can go shopping in a simulated or virtual reality environment.

In each of these presentations, as the shopper 610 views each individual product 620A, 620B, 620C, 620D on the shelf, the eye tracking system can determine which product is being focused on and the biometric responses of the user can be recorded at that time. The response data, when it is stored, can be associated with a time mark, frame number, or an arbitrary index mark or number of the presentation. In one embodiment, the system records the responses on 20 ms intervals, but longer or shorter intervals can be used depending on the various constraints and requirements of the system, for example, the speed and size of the data storage system and the response characteristics of the sensor systems being used and the desired resolution. In accordance with one embodiment of the invention, the presentation can provide running time or a frame by frame index or time that allows the system to associate the response data with a specific point in time, typically offset from the beginning of the presentation or allows the response data to be associated with a specific frame number or time index associated with a specific frame.

In other embodiments of the invention, the presentation can be marked or associated with predefined event windows that start at a predefined time or frame of the presentation and extend for a predefined duration of time. The time between event windows does not have to be constant and the duration of an event window can be the same or different from one event window to the next. In one embodiment, an event window begins when a user is presented with a screen display which involves the user in an interactive presentation, task or activity and extends for a duration of five (or in some cases, up to ten) seconds. During the five (or ten) second window, the eye tracking, behavior and biometric response data can be collected on 20 ms intervals, providing up to 250 (or 500 for 10 second duration) data points from each sensor for the event window. Some sensors may not provide data at the same frequency and the system can determine a single elemental value for each response measured on an event window by event window basis. The single elemental value for the event window can, for example, be determined as function of the mean, median or mode of the response data received during the time period corresponding to the event window.

In accordance with one embodiment of the invention, the above metrics can be used to analyze the engagement and visual impact of various interactive and passive presentations for various audiences. It has been found that the high visual impact index correlates well with the biometric non-visual intensity (using non-visual, biometric responses, e.g., heart rate, skin conductivity, respiration) at the time of purchase or product selection whereas the low visual impact index correlates well with the biometric non-visual intensity at the time of returning products back on product shelf.

The Flow index of a task, process or experience can be determined as a function of measures of task (process, or experience) completion indices, efficiency indices and frustration indices and can include self-report and biometric responses to further weight or adjust the completion index, efficiency index and frustration index. In accordance with one embodiment of the invention, the Flow Index can be determined by the equation:

Flow Index=(Completion Index+Efficiency Index)−Frustration Index

The Completion index can be determined as a function of the percentage of a test group of individual users that completed a task, process or experience and one or more metrics relating to the time to completion, such as the mean time to completion and the standard deviation over the test group. Tasks or processes that have a high percentage of completion can be given a high completion index, and where two or more tasks have a similar percentage of completion, the tasks with shortest time to completion or the smallest deviation in time to completion can be weighted higher than the others.

If compl-time(T) represents the mean time for completion of task T, then completion index for task T can be defined as a z-score, such as (compl-time($T$)−average of (compl-time($Ti$)))/Standard_deviation(compl_time($Ti$).

Other functions for the Completion index of task T can also be derived, using predictive models described in the data mining hooks described herein, by relating the completion times to outcome variables such as test groups behavior (e.g., like/dislike of a task T). Specific techniques that could be utilized include regression analysis for finding a relationship between completion times and outcome variables and using completion index as an indicator of the outcome variable.

The Efficiency index can be determined as a function of gaze fixation and duration over a series of one or more target areas of interest (such as along a task path). The Efficiency index can be weighted by a self-report measure of ease-of-use and user experience. Tasks or processes that have a higher percentage of gaze fixation and duration on the predefined target areas can be given a higher efficiency index and this value can be weighted based on the self report responses to questions and inquiries relating to ease of use and user experience.

> Efficiency Index for task $T$ with target area set $A$=Emotive Efficiency Index for $T$ with target area set $A$+Cognitive efficiency Index for $T$ with target area set $A$ Where Cognitive efficiency index for task T with target set A=High cognitive efficiency index for T with target set A if >0
Otherwise, Low cognitive efficiency index for T with A
High cognitive efficiency index for T with A=sum of areas (geometric intersection of (high cognitive map, A)/Sum of plot areas in high cognitive map.
Low cognitive efficiency index for T with A=(−1)*sum of areas (geometric intersection of (high cognitive map, A)/Sum of plot areas in high cognitive map
Emotive efficiency index for task T with target set A=High emotive efficiency index for T with target set A if >0
Otherwise, Low emotive efficiency index for T with A
High emotive efficiency index for T with A=sum of areas (geometric intersection of (high emotive map, A)/Sum of plot areas in high emotive map
Low emotive efficiency index for T with A=(−1)*sum of areas (geometric intersection of (high emotive map, A)/Sum of plot areas in high emotive map
Other functions for combining the high/low emotive, cognitive efficiency indexes can also be derived using predictive models, described in the data mining books described herein, by relating the efficiency indexes to outcome variables such as the test group's behavior (e.g., like/dislike of a task T). Specific techniques that could be utilized include regression analysis for finding a relationship between completion times and outcome variables and using efficiency index as an indicator of the outcome variable.

The Frustration index can be determined as a function of behavioral responses that tend to indicate frustration, such as facial expressions and body movements and system input devices that can measure pressure, such as a pressure sensing computer mouse or other input device (for example, pressure and repetition of key presses applied to the keys of a keyboard). The frustration index can be weighted by one or more of a self-report measure of frustration and one or more biometric emotive measures.

> Frustration index for task $T$=Sum of frustration indexes from pressure mouse responses, body movement, key presses, and facial expressions; and
>
> Frustration index for task $T$ from pressure mouse=$z$-score of pressure mouse signals for task $T$ in comparison to a database of tasks $T$-DB.

Likewise, Frustration index for task T from key presses-z-score of key presses for task T in comparison to a database of tasks T-DB.

The frustration index can also be restricted to specific target areas mentioned in self-report studies. For instance frustration index for task T from key presses in target area set A can only account for the key presses within the target area set A.

Other functions for frustration index for Task T can also be derived using predictive models, described in the data mining books described herein, by relating the input variables (key presses, pressure mouse signal values, etc.) to outcome variables such as test group's behavior (e.g., like/dislike of a task T). Specific techniques that could be utilized include regression analysis for finding a relationship between input and outcome variables and assuming frustration index as an indicator of the outcome variable.

The Appeal index of a task, process or experience can be determined as a function of a weighted combination (of one or more) of self report responses for likeability, biometric emotive responses, and behavioral measures of micro and macro facial expressions, body or head lean toward the activity. The Appeal index can provide an indication of attractiveness by the user to the task, process or experience, with a high appeal index indicating a more enjoyable experience.

> Appeal index for $T$=sum of (weight($s$)*self report($T$), weight($b1$)*biometric responses($T,b1$), weight ($bn$)*biometric responses($T,bn$)), for $i$=1 to $n$.

Where bi is the ith biometric measure of n biometric measures.

Other functions for appeal index for Task T can also be derived using predictive models, described in the data mining books described herein, by relating the input variables (self report, head lean values, etc.) to outcome variables such as test group's behavior (e.g., like/dislike of a task T). Specific techniques that could be utilized include regression analysis for finding a relationship between input and outcome variables.

The Engagement index of a task, process or experience can be determined as a function of the Flow index, Appeal index, Biometric Emotive Power index and Biometric Cognitive Power index, for example:

> Engagement Index=Flow Index+Appeal Index+Biometric Emotive Power Index+Biometric Cognitive Power Index In addition, Biometric Persona or groupings can be created by identifying a group of users having a similarity of their pattern of task, process or experience metrics without regard to demographic or psychographic profile. Note that this grouping can utilize machine-based clustering algorithms for this grouping, or alternately may involve a manual process of an administrator/expert identifying the groupings or clusters of users.

Other embodiments are within the scope and spirit of the invention. For example, due to the nature of the scoring algorithm, functions described above can be implemented and/or automated using software, hardware, firmware, hardwiring, or combinations of any of these. Features implementing the functions can also be physically located at various positions, including being distributed such that the functions or portions of functions are implemented at different physical locations.

Further, while the description above refers to the invention, the description may include more than one invention.

What is claimed is:
1. A system for determining a measure of response of an audience to a target stimulus comprising:

at least one display device to display a first set of stimuli to the audience;

at least one sensor to measure at least two biometric parameters of a plurality of participants in the audience measured during a plurality of exposures of the first set of stimuli to each participant in the audience, wherein the first set of stimuli comprise:

a first series of standardized stimuli, wherein each standardized image is followed by a null exposure, a first target stimulus, wherein the target stimulus is followed by a null exposure, a second series of standardized stimuli, wherein each standardized image is followed by a null exposure, and re-exposure to each target stimulus;

at least one self-report device to collect self-report responses from the plurality of members of the audience;

a first processor;

memory connected to the first processor storing program instructions and data;

program instructions stored in the memory and executable by the first processor to:

(1) receive data from the at least one sensor, the data representative of the at least two biometric parameters measured during the plurality of exposures of the first set of stimuli to each participant in the audience;

(2) determine response synchrony of the audience by:
stamping the data from the at least one sensor for each participant with a time indicator and a participant identifier;
synchronizing the data from the at least one sensor for each participant with the first presentation;
measuring a rate of change of the data from the at least one sensor during a first time period in the first presentation; and
standardizing the data received from the at least one sensor for the audience based on the rate of change during the first time period, the standardized data representative of the response synchrony;

(3) determine an Emotional Impact Score by calculating a single physiological score for each participant based on the received data representative of the at least two biometric parameters, wherein the single physiological score comprises an integration across channels of the at least two biometric parameters; and (4) calculate an Explicit Emotion Score for the audience using each participant's response to the at least one self-report question; and a second processor, the first processor to transmit the Emotional Impact Score and the Explicit Emotion Score to the second processor, the second processor to:
plot the Emotional Impact Score and the Explicit Emotion Score on a biphasic graph to predict a level of engagement of a population larger than the audience;
estimate an effectiveness of the first set of stimuli based on the level of engagement; and
select at least one of (1) elements of the first set of stimuli or (2) a second set of stimuli for subsequent presentation based on the estimate.

2. The system of claim 1, wherein the audience comprises at least 10 participants.

3. The system of claim 1, wherein the at least one self-report question comprises a level of likeability of the at least one target stimulus, a valence of emotional response to the at least one target stimulus, an interest for the at least one target stimulus, or a combination thereof.

4. The system of claim 1, wherein the at least one self-report question comprises at least three self-report questions.

5. The system of claim 4, wherein the Explicit Emotion Score for the audience is calculated using each participant's response to the at least three self-report questions.

6. The system of claim 1, wherein the at least one self-report question comprises at least three self-report questions comprising a level of likeability of the at least one target stimulus, a valence of emotional response to the at least one target stimulus, and an interest for the at least one target stimulus.

7. The system of claim 1, wherein each participant is exposed to the standardized stimuli and the at least one target stimulus for between about 5 seconds and about 20 seconds, and wherein each participant is exposed to a null exposure for between about 5 seconds and about 15 seconds.

8. The system of claim 1, wherein the at least two parameters each independently comprise one of skin conductance, heart rate, heart rate variability respiration, and brain wave activity.

9. The system of claim 1, wherein the first processor is to receive visual attention data from each participant via a visual attention device, wherein the at least one biometric sensor, the visual attention device, and the display device are synchronized.

10. A computer program product for determining a measure of response of an audience to a target stimulus comprising a non-transitory computer readable medium storing computer program instructions executable by a first processor to perform:

(1) measuring, using at least one sensor, at least two biometric parameters of a plurality of participants in the audience measured during a first presentation displayed by a display device to the audience presented over a period of time, the first presentation including a first series of standardized stimuli, at least one target stimulus, and a second series of standardized stimuli, and, using the at least one sensor, the at least two biometric parameters measuring during a re-exposure of the audience to the at least one target stimulus;

(2) receiving data from the at least one sensor, the data including data representative of the at least two biometric parameters collected during the first presentation to the audience;

(3) determining response synchrony of the audience by:
stamping the data from the at least one sensor for each participant with a time indicator and a participant identifier;
synchronizing the data from the at least one sensor for each participant with the first presentation;
measuring a rate of change of the data from the at least one sensor during a first time period in the first presentation; and
standardizing the data received from the at least one sensor for the audience based on the rate of change during the first time period, the standardized data representative of the response synchrony;

(4) determining an Emotional Impact Score by calculating a single physiological score for each participant based on the received data representative of the at least two biometric parameters;

(5) calculating an Explicit Emotion Score by: collecting and recording from the at least one self-report device for each participant a response to at least one self-report question during the re-exposure, wherein the at least one self-report question comprises a level of likeability of the at least one target stimulus, a valence of emotional response to the at least one target stimulus, an interest for the at least one target stimulus, or a combination thereof, wherein the Explicit Emotion Score comprises a single score comprising a combination of the responses to each of the at least one self-report question; and (6) transmitting the Emotional Impact Score and the Explicit Emotion Score to a second processor, wherein the second processor is to:
  plot the Emotional Impact Score and the Explicit Emotion Score on a biphasic graph to predict a level of engagement of a population larger than the audience;
  estimate an effectiveness of the first presentation based on the level of engagement; and
  select at least one of (1) elements of the first presentation or (2) a second presentation for subsequent presentation based on the estimate.

11. A computer program product for determining a measure of response of an audience to a target stimulus comprising a non-transitory computer readable medium storing computer program instructions executable by a first processor to perform:
  (1) measuring, using at least one sensor, at least two biometric parameters of a plurality of participants in the audience measured during a plurality of exposures of a first set of stimuli to each participant in the audience, wherein the first set of stimuli comprise:
    a first series of standardized stimuli, wherein each standardized image is followed by a null exposure,
    a first target stimulus, wherein the target stimulus is followed by a null exposure,
    a second series of standardized stimuli, wherein each standardized image is followed by a null exposure, and
    re-exposure to each target stimulus;
  (2) receiving data representative of at least two biometric parameters measured during the plurality of exposures of the first set of stimuli to each participant in the audience;
  (3) determining response synchrony of the audience by:
    stamping the data from the at least one sensor for each participant with a time indicator and a participant identifier;
    synchronizing the data from the at least one sensor for each participant with the first presentation;
    measuring a rate of change of the data from the at least one sensor during a first time period in the first presentation; and
    standardizing the data received from the at least one sensor for the audience based on the rate of change during the first time period, the standardized data representative of the response synchrony;
  (4) determining an Emotional Impact Score by calculating a single physiological score for each participant based on the received data representative of the at least two biometric parameters, wherein the single physiological score comprises an integration across channels of the at least two biometric parameters;
  (5) calculating an Explicit Emotion Score for the audience using each participant's response to the at least one self-report question; and (6) transmitting the Emotional Impact Score and the Explicit Emotion Score to a second processor, wherein the second processor is to:
    plot the Emotional Impact Score and the Explicit Emotion Score on a biphasic graph to predict a level of engagement of a population larger than the audience;
    estimate an effectiveness of the first set of stimuli based on the level of engagement; and
    select at least one of (1) elements of the first set of stimuli or (2) a second set of stimuli for subsequent presentation based on the estimate.

12. A system for determining a measure of response of an audience to a target stimulus comprising:
  at least one display device to display a first presentation to the audience;
  at least one sensor to measure at least two biometric parameters of a plurality of participants in the audience measured during the first presentation displayed by the display device to the audience presented over a period of time, the first presentation including a first series of standardized stimuli, at least one target stimulus, and a second series of standardized stimuli, and measured during a re-exposure of the audience to the at least one target stimulus;
  at least one self-report device to collect self-report responses from the plurality of members of the audience;
  a first processor;
  memory connected to the first processor storing program instructions and data;
  program instructions stored in the memory and executable by the first processor to:
    (1) receive data from the at least one sensor, the data including data representative of the at least two biometric parameters measured during the first presentation to the audience;
    (2) determine response synchrony of the audience by:
      stamping the data from the at least one sensor for each participant with a time indicator and a participant identifier;
      synchronizing the data from the at least one sensor for each participant with the first presentation;
      measuring a rate of change of the data from the at least one sensor during a first time period in the first presentation; and
      standardizing the data received from the at least one sensor for the audience based on the rate of change during the first time period, the standardized data representative of the response synchrony;
    (3) determine an Emotional Impact Score by calculating a single physiological score for each participant based on the received data representative of the at least two biometric parameters; and
    (4) calculate an Explicit Emotion Score by: collecting and recording from the at least one self-report device for each participant a response to at least one self-report question during the re-exposure, wherein the at least one self-report question comprises a level of likeability of the at least one target stimulus, a valence of emotional response to the at least one target stimulus, an interest for the at least one target stimulus, or a combination thereof, wherein the Explicit Emotion Score comprises a single score comprising a combination of the responses to each of the at least one self-report question; and a second processor, the first processor to transmit the Emotional Impact Score and the Explicit Emotion Score to the second processor, the second processor to:
plot the Emotional Impact Score and the Explicit Emotion Score on a biphasic graph to predict a level of engagement of a population larger than the audience;
estimate an effectiveness of the first presentation based on the level of engagement; and
select at least one of (1) elements of the first presentation or (2) a second presentation for subsequent presentation based on the estimate.

13. The system of claim 12, wherein the second processor is to estimate the effectiveness of the first presentation by comparing the level of engagement for the first presentation to a level of engagement for a third presentation, the third presentation occurring at an earlier time than the presentation.

14. The system of claim 13, further including identifying an shared attribute between the first presentation and the third presentation based on the estimate.

15. The system of claim 12, wherein the first processor is to transmit the response synchrony to the second processor and the second processor is to predict the level of engagement based also on the response synchrony.

16. The system of claim 12, wherein the first series of standardized stimuli comprises between 4 and 20 standardized images and wherein the second series of standardized stimuli comprises between 4 and 20 standardized images.

17. The system of claim 12, wherein data representative of a third biometric parameter is received.

18. The system of claim 12, wherein the at least two biometric parameters include a first and a second biometric parameter, wherein each parameter independently comprises one of skin conductance, heart rate, heart rate variability respiration, and brain wave activity.

19. The system of claim 12, wherein the system further receives visual attention data collected during the first presentation and the re-exposure, and the single physiological score for each participant is further based on the received visual attention data.

20. The system of claim 19, wherein the visual attention data comprises at least one of gaze location, fixation duration, and movement over the first presentation for each member of the audience.

21. The system of claim 12, wherein the at least two biometric parameters each independently comprise one of skin conductance, heart rate, heart rate variability respiration, and brain wave activity.

* * * * *